(12) United States Patent
Oberholzer

(10) Patent No.: US 9,688,639 B2
(45) Date of Patent: Jun. 27, 2017

(54) SOLID FORMS OF FUNGICIDAL PYRAZOLES

(71) Applicant: E. I. DU PONT DE NEMOURS AND COMPANY, Wilmington, DE (US)

(72) Inventor: Matthew Richard Oberholzer, Wilmington (DE)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/888,835

(22) PCT Filed: May 15, 2014

(86) PCT No.: PCT/US2014/038132
§ 371 (c)(1),
(2) Date: Nov. 3, 2015

(87) PCT Pub. No.: WO2014/189753
PCT Pub. Date: Nov. 27, 2014

(65) Prior Publication Data
US 2016/0075661 A1 Mar. 17, 2016

Related U.S. Application Data

(60) Provisional application No. 61/825,139, filed on May 20, 2013.

(51) Int. Cl.
*C07D 231/38* (2006.01)
*A01N 43/56* (2006.01)

(52) U.S. Cl.
CPC ............ *C07D 231/38* (2013.01); *A01N 43/56* (2013.01)

(58) Field of Classification Search
None
See application file for complete search history.

(56) References Cited

U.S. PATENT DOCUMENTS

2015/0018374 A1* 1/2015 Taggi et al. ............ A01N 43/56
514/255.06

FOREIGN PATENT DOCUMENTS

| WO | 2012031061 A2 | 3/2012 |
| WO | 2013116251 A2 | 8/2013 |

OTHER PUBLICATIONS

Bavin, Chemistry & Industry, vol. 21, No. 16, 1989, pp. 527-529.
Caira, Topics in Current Chemistry, vol. 198, 1998, pp. 163-208.

* cited by examiner

*Primary Examiner* — Kamal Saeed
(74) *Attorney, Agent, or Firm* — Charlene Gross Sternberg

(57) ABSTRACT

Disclosed are solid forms of 4-(2-bromo-4-fluorophenyl)-N-(2-chloro-6-fluorophenyl)-1,3-dimethyl-1H-pyrazol-5-amine (Compound 1). Methods for the preparation of solid forms of Compound 1 and for the conversion of one solid form of Compound 1 into another are disclosed.

Disclosed are compositions for protecting a plant or plant seed from diseases caused by fungal pathogens comprising a biologically effective amount of a solid form of Compound 1 and at least one additional component selected from the group consisting of surfactants, solid diluents and liquid carriers. Compositions comprising a mixture of a solid form of Compound 1 and at least one other nematocide, insecticide and/or fungicide are also disclosed.

Also disclosed are methods for protecting a plant or plant seed from diseases caused by fungal pathogens comprising applying to a plant or seed, or to the environment of the plant or seed, a biologically effective amount of a solid form of Compound 1.

16 Claims, 2 Drawing Sheets

SOLID FORMS OF FUNGICIDAL PYRAZOLES

FIELD OF THE INVENTION

This invention relates to solid forms of 4-(2-bromo-4-fluorophenyl)-N-(2-chloro-6-fluorophenyl)-1,3-dimethyl-1H-pyrazol-5-amine, their preparation, compositions, and methods of use for protecting a plant or plant seed from diseases caused by fungal pathogens.

BACKGROUND OF THE INVENTION

The solid state of chemical compounds can be amorphous (i.e. no long-range order in the positions of atoms) or crystalline (i.e. atoms arranged in an orderly repeating pattern). The term "polymorph" refers to a particular crystal form (i.e. structure of crystal lattice) of a chemical compound that can exist in more than one crystal form in the solid state. Polymorphs can differ in such chemical and physical (i.e. physicochemical) properties as crystal shape, density, hardness, color, chemical stability, melting point, hygroscopicity, suspensibility, solubility and dissolution rate, and such biological properties as biological availability, biological efficacy and toxicity.

Predicting physicochemical properties such as melting point or solubility for a crystal form in which the solid state of a chemical compound can exist remains impossible. Furthermore, even predicting whether the solid state of a compound may be present in more than one crystal form is not possible.

PCT Patent Publication WO 2012/031061 discloses 4-(2-bromo-4-fluorophenyl)-N-(2-chloro-6-fluorophenyl)-1,3-dimethyl-1H-pyrazol-5-amine and methods for its preparation, as well as the utility of this compound for protecting a plant or plant seed from diseases caused by fungal pathogens. New solid forms of this compound, their compositions and methods of their preparation and use have now been discovered.

SUMMARY OF THE INVENTION

This invention relates to solid forms of 4-(2-bromo-4-fluorophenyl)-N-(2-chloro-6-fluorophenyl)-1,3-dimethyl-1H-pyrazol-5-amine (Compound 1). More particularly, this invention is directed to a polymorph of Compound 1 designated Form A characterized by room-temperature powder Cu(K$\alpha$1)-X-ray diffraction pattern having at least the 2$\theta$ reflection positions 6.395, 12.668, 14.507, 14.99, 18.984, 22.23, 23.885, 24.919 and 26.34 degrees. This invention is also particularly directed to a polymorph of Compound 1 designated Form B characterized by room-temperature powder Cu(K$\alpha$1)-X-ray diffraction pattern having at least the 2$\theta$ reflection positions 10.894, 15.361, 16.134, 17.718, 20.322, 24.285, 25.84, 27.54 and 29.449 degrees.

This invention relates to methods for the conversion of one solid form of Compound 1 into polymorph Form B. More particularly, this invention is directed to a method for preparing a polymorph of Compound 1 designated Form B, the method comprising: forming a slurry with a solvent of one or more solid forms of Compound 1 selected from the group of Form A, amorphous forms and mixtures thereof with Form B and maintaining the slurry while the solid forms of Compound 1 convert to polymorph Form B.

This invention also relates to methods for preparing polymorph Form B of Compound 1 comprising, (A) contacting 1-(2-bromo-4-fluorophenyl)-2-propanone and 1-chloro-3-fluoro-2-isothiocyanatobenzene in the presence of a first solvent to form a reaction mixture containing a thioamide intermediate, (B) optionally isolating the thioamide intermediate, (C) contacting the thioamide intermediate with methylhydrazine in the presence of a second solvent to form a reaction mixture containing Compound 1, and (D) crystallizing the Compound 1 as the polymorph Form B.

This invention also relates to a composition for protecting a plant or plant seed from diseases caused by fungal pathogens comprising (a) polymorph Form B of Compound 1; and (b) at least one additional component selected from the group consisting of surfactants, solid diluents and liquid carriers.

This invention also relates to a composition for protecting a plant or plant seed from diseases caused by fungal pathogens comprising (a) polymorph Form B of Compound 1; and (b) at least one other nematocide, insecticide and/or fungicide.

This invention further relates to a method of use for protecting a plant or plant seed from diseases caused by fungal pathogens comprising applying to a plant or seed, or to the environment of the plant or seed, a biologically effective amount of Compound 1 comprising the polymorph Form B.

DETAILED DESCRIPTION OF THE INVENTION

Figure 1A:
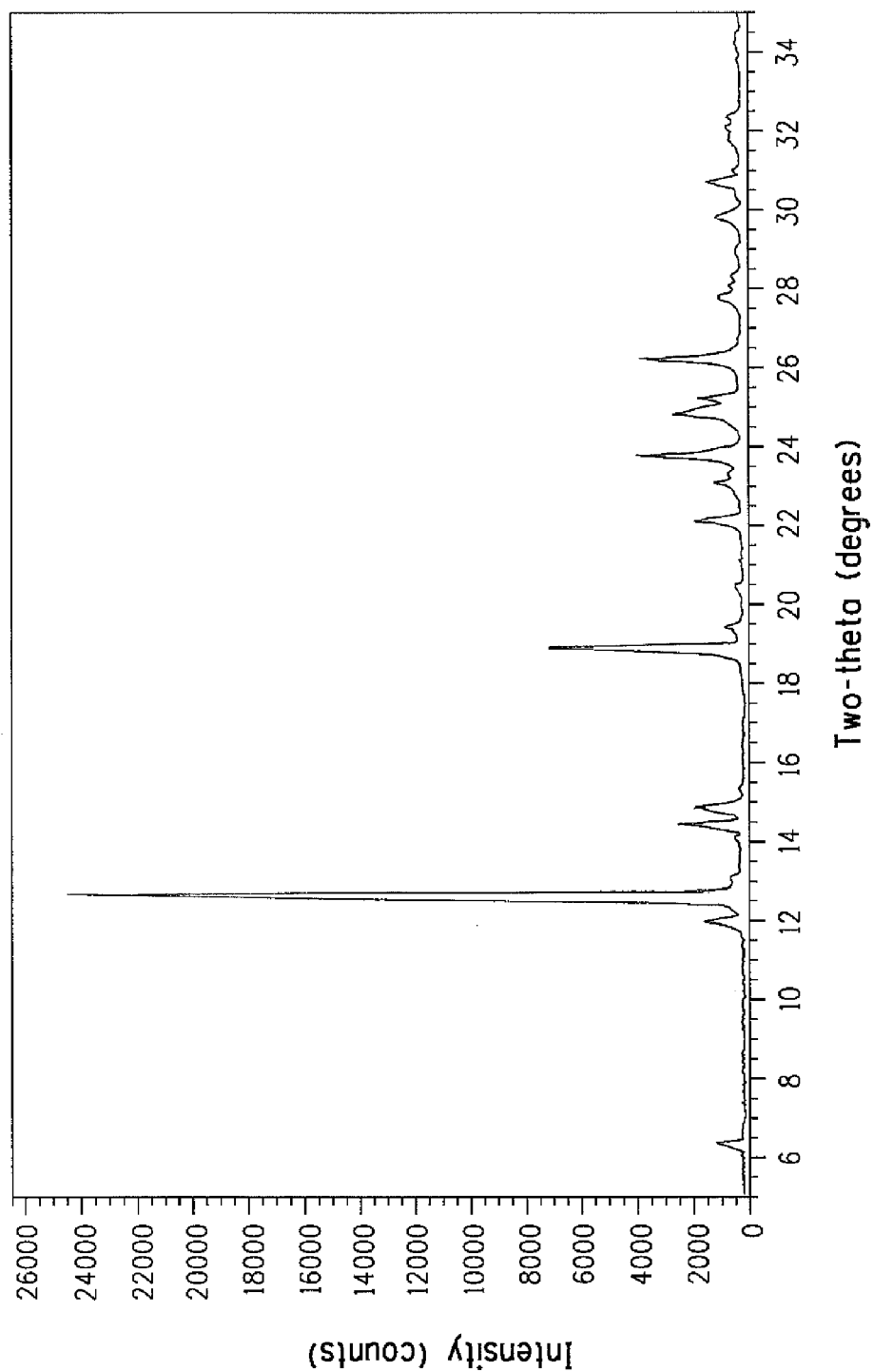
FIG. 1A shows room temperature Cu-K$\alpha$1-powder X-ray diffraction patterns of polymorph Form A of Compound 1 showing absolute X-ray intensity in counts graphed against 2$\theta$ reflection positions in degrees.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda.

In the context of this disclosure "invertebrate pest control" means inhibition of invertebrate pest development (including mortality, feeding reduction, and/or mating disruption), and related expressions are defined analogously.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium such as roots, tubers, bulbs and corms, and also members growing above the growing medium, such as foliage (including stems and leaves), flowers, fruits and seeds. Growing mediums include soil, liquid nutrient mediums, gel nutrient mediums or soil mixes with peat, bark, saw dust, sand, pumice, perlite, vermiculite and other similar products. As referred to herein, the term "seedling", used either alone or in a combination of words means a young plant developing from the embryo of a seed.

As referred to in this disclosure, the term "fungal pathogen" or "fungal plant pathogen" includes pathogens in the Basidiomycete, Ascomycete, Oomycete and Deuteromycete classes that are the causal agents of a broad spectrum of plant diseases of economic importance, affecting ornamental, turf, vegetable, field, cereal, and fruit crops. In the context of this disclosure "protecting a plant from disease", "plant disease control" or "fungal pathogen control" includes preventative action (interruption of the fungal cycle of infection, colonization, symptom development and spore production) and/or curative action (inhibition of the colonization of plant host tissues).

The term "water-miscible" in the context of "water-miscible solvent" means a liquid solvent (including mixtures of solvent compounds) that is completely soluble in water (and water soluble in the solvent) in all proportions at the temperature of the (e.g., reaction) medium comprising the water-miscible solvent. Methanol, ethanol, acetone and acetonitrile are examples of water-miscible solvents.

Conversely, the term "water-immiscible" in the context of a substance that is a "water-immiscible organic compound", "water-immiscible liquid component" or "water-immiscible liquid carrier" denotes that the substance is not soluble in water (and water soluble in the substance) in all proportions at relevant temperatures (for formulated compositions around room temperature, e.g. about 20° C.). Typically water-immiscible substances used as liquid carriers or other liquid components in formulated compositions have little water solubility and water has little solubility in the water-immiscible substances. Often water-immiscible substances used in formulation are soluble in water in an extent of less than about 1%, or less than about 0.1%, or even less than about 0.01% by weight at about 20° C.

The expression "continuous liquid phase" in the context of liquid formulated compositions refers to the liquid phase formed by the liquid carrier. The continuous liquid phase provides the bulk liquid medium in which other formulating components are dissolved, dispersed (as solid particulates) or emulsified (as liquid droplets). When the liquid carrier is aqueous (water optionally containing dissolved water-soluble compounds), a liquid emulsified in the aqueous liquid carrier is formed by a water-immiscible liquid component.

The term "room temperature" as used in this disclosure refers to a temperature between about 18° C. and about 28° C.

The term "polymorph" refers to a particular crystal form (i.e. structure of crystal lattice) of a chemical compound that can exist in more than one crystal form in the solid state.

Embodiments of the present invention include:

Embodiment 1

The polymorph of 4-(2-bromo-4-fluorophenyl)-N-(2-chloro-6-fluorophenyl)-1,3-dimethyl-1H-pyrazol-5-amine (Compound 1) designated Form A in the Summary of the Invention and characterized by room-temperature powder Cu(Kα1)-X-ray diffraction pattern having at least the 2θ reflection positions

| 2θ |
| --- |
| 6.395 |
| 12.668 |
| 14.507 |
| 14.99 |
| 18.984 |
| 22.23 |
| 23.885 |
| 24.919 |
| 26.34. |

Embodiment 2

The polymorph of 4-(2-bromo-4-fluorophenyl)-N-(2-chloro-6-fluorophenyl)-1,3-dimethyl-1H-pyrazol-5-amine (Compound 1) designated Form B in the Summary of the Invention and characterized by room-temperature powder Cu(Kα1)-X-ray diffraction pattern having at least the 2θ reflection positions

| 2θ |
| --- |
| 10.894 |
| 15.361 |
| 16.134 |
| 17.718 |
| 20.322 |

-continued

| 2θ |
|---|
| 24.285 |
| 25.84 |
| 27.54 |
| 29.449. |

Embodiment 3

The method described in the Summary of the Invention for preparing the polymorph Form B of Embodiment 2 comprising forming a slurry with a solvent of one or more solid forms of Compound 1 selected from the group of Form A, amorphous forms and mixtures of any of the foregoing with Form B and maintaining the slurry while the solid forms of Compound 1 convert to polymorph Form B.

Embodiment 4

The method of Embodiment 3 wherein the solid form of Compound 1 comprises polymorph Form A.

Embodiment 5

The method of Embodiment 3 wherein the solid forms of Compound 1 comprises a mixture of polymorphs Form A and Form B.

Embodiment 6

The method of any one of Embodiments 3 through 5 wherein seed crystals of polymorph Form B of Embodiment 2 are added to the slurry.

Embodiment 7

The method of any one of Embodiments 3 through 6 wherein the slurry is agitated.

Embodiment 8

The method of any one of Embodiments 3 through 6 wherein the slurry is agitated and heated to a temperature between 30° C. and the boiling point of the solvent.

Embodiment 9

The method of any one of Embodiments 3 through 8 wherein the solvent comprises one or more of water, a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

Embodiment 10

The method of Embodiment 9 wherein the solvent comprises one or more of water, butyl acetate, methanol, 1-propanol or toluene.

Embodiment 11

The method of Embodiment 10 wherein the solvent comprises one or more of water or methanol.

Embodiment 12

The method described in the Summary of the Invention for preparing a crystalline form of Compound 1 comprising, (A) contacting 1-(2-bromo-4-fluorophenyl)-2-propanone and 1-chloro-3-fluoro-2-isothiocyanatobenzene in the presence of a first solvent to form a reaction mixture containing a thioamide intermediate, (B) optionally isolating the thioamide intermediate, (C) contacting the thioamide intermediate with methylhydrazine in the presence of a second solvent to form a reaction mixture containing Compound 1, and (D) crystallizing the Compound 1 as the polymorph Form B.

Embodiment 13

The method of Embodiment 12 wherein the thioamide intermediate is isolated in step (B).

Embodiment 14

The method of Embodiment 12 wherein the thioamide intermediate is not isolated in step (B).

Embodiment 15

The method of any one of Embodiments 12 through 14 wherein the thioamide intermediate is α-acetyl-2-bromo-N-(2-chloro-6-fluorophenyl)-4-fluorobenzeneethanethioamide.

Embodiment 16

The method of any one of Embodiments 12 through 15 wherein the first solvent comprises one or more of a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

Embodiment 17

The method of Embodiment 16 wherein the first solvent comprises one or more of tetrahydrofuran or methyl tert-butylether.

Embodiment 18

The method of any one of Embodiments 12 through 17 wherein the first solvent is cooled to a temperature between 0° C. and 15° C.

Embodiment 19

The method of any one of Embodiments 12 through 18 wherein the second solvent comprises one or more of water, a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

Embodiment 20

The method of Embodiment 19 wherein the second solvent comprises one or more of tetrahydrofuran, toluene, methanol or ethanol.

Embodiment 21

The method of any one of Embodiments 12 through 20 wherein the second solvent is heated to a temperature between 30° C. and the boiling point of the second solvent.

Embodiment 22

The method of any one of Embodiments 12 through 21 wherein the first solvent and the second solvent are the same.

Embodiment 23

The method of any one of Embodiments 12 through 22 wherein in step (D) Compound 1 is crystallized in the presence of seed crystals of polymorph Form B.

Embodiment 24

The method of any one of Embodiments 12 through 22 wherein in step (D) Compound 1 is crystallized in the presence of a third solvent and seed crystals of polymorph Form B.

Embodiment 25

The method of Embodiment 24 wherein the third solvent comprises one or more of water, a $C_1$-$C_4$ alkanol, a $C_5$-$C_8$ hydrocarbon or a $C_7$-$C_9$ aromatic hydrocarbon.

Embodiment 26

The method of Embodiment 25 wherein the third solvent comprises one or both of water or methanol.

Embodiment 27

The method described in the Summary of the Invention for preparing a crystalline form of Compound 1 comprising, (A) contacting 1-(2-bromo-4-fluorophenyl)-2-propanone and 1-chloro-3-fluoro-2-isothiocyanatobenzene in the presence of a first solvent to form a reaction mixture containing a condensation product salt, (B) contacting the condensation product salt with an alkylating agent to form an alkylated thioamide intermediate, (C) optionally isolating the alkylated thioamide intermediate, (D) contacting the alkylated thioamide intermediate with methylhydrazine in the presence of a second solvent to form a reaction mixture containing Compound 1 and (E) crystallizing the Compound 1 as the polymorph Form B.

Embodiment 28

The method of Embodiment 27 wherein the alkylated thioamide intermediate is isolated in step (B).

Embodiment 29

The method of Embodiment 27 wherein the alkylated thioamide intermediate is not isolated in step (B).

Embodiment 30

The method of any one of Embodiments 27 through 29 wherein the alkylated thioamide intermediate is 3-(2-bromo-4-fluorophenyl)-4-[(2-chloro-6-fluorophenyl)amino]-4-(methylthio)-3-buten-2-one.

Embodiment 31

The method of any one of Embodiments 27 through 30 wherein the first solvent comprises one or more of a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

Embodiment 32

The method of Embodiment 31 wherein the first solvent comprises one or more of tetrahydrofuran or methyl tert-butylether.

Embodiment 33

The method of any one of Embodiments 27 through 32 wherein the first solvent is cooled to a temperature between 0° C. and 15° C.

Embodiment 34

The method of any one of Embodiments 27 through 33 wherein the second solvent comprises one or more of water, a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

Embodiment 35

The method of Embodiment 34 wherein the second solvent comprises one or more of tetrahydrofuran, toluene, methanol or ethanol.

Embodiment 36

The method of any one of Embodiments 27 through 35 wherein the second solvent is heated to a temperature between 30° C. and the boiling point of the second solvent.

Embodiment 37

The method of any one of Embodiments 27 through 36 wherein the first solvent and the second solvent are the same.

Embodiment 38

The method of any one of Embodiments 27 through 37 wherein in step (D) Compound 1 is crystallized in the presence of seed crystals of polymorph Form B.

Embodiment 39

The method of any one of Embodiments 27 through 37 wherein in step (D) Compound 1 is crystallized in the presence of a third solvent and seed crystals of polymorph Form B.

Embodiment 40

The method of Embodiment 39 wherein the third solvent comprises one or more of water, a $C_1$-$C_4$ alkanol, a $C_5$-$C_8$ hydrocarbon or a $C_7$-$C_9$ aromatic hydrocarbon.

Embodiment 41

The method of Embodiment 40 wherein the third solvent comprises one or both of water or methanol.

Embodiment 42

The composition described in the Summary of the Invention for protecting a plant or plant seed from diseases caused by fungal pathogens comprising (a) polymorph Form A of Compound 1; and (b) at least one additional component selected from the group consisting of surfactants, solid diluents and liquid carriers.

Embodiment 43

The composition described in the Summary of the Invention for protecting a plant or plant seed from diseases caused by fungal pathogens comprising (a) polymorph Form B of Compound 1; and (b) at least one additional component selected from the group consisting of surfactants, solid diluents and liquid carriers.

Embodiment 44

The composition described in the Summary of the Invention for protecting a plant or plant seed from diseases caused by fungal pathogens comprising (a) polymorph Form A of Compound 1; and (b) at least one other nematocide, insecticide and/or fungicide.

Embodiment 45

The composition described in the Summary of the Invention for protecting a plant or plant seed from diseases caused by fungal pathogens comprising (a) polymorph Form B of Compound 1; and (b) at least one other nematocide, insecticide and/or fungicide.

Embodiment 46

The method of use described in the Summary of the Invention for protecting a plant or plant seed from diseases caused by fungal pathogens comprising applying to a plant or seed, or to the environment of the plant or seed, a biologically effective amount of Compound 1 comprising the polymorph Form A.

Embodiment 47

The method of use described in the Summary of the Invention for protecting a plant or plant seed from diseases caused by fungal pathogens comprising applying to a plant or seed, or to the environment of the plant or seed, a biologically effective amount of Compound 1 comprising the polymorph Form B.

Embodiments of this invention, including Embodiments 1-47 above as well as any other embodiments described herein, can be combined in any manner.

Compound 1 is 4-(2-bromo-4-fluorophenyl)-N-(2-chloro-6-fluorophenyl)-1,3-dimethyl-1H-pyrazol-5-amine and has the following molecular structure:

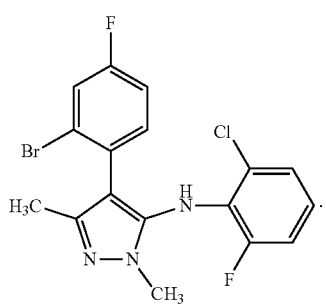

1

The solid state of Compound 1 has now been discovered to be preparable in more than one solid form. These solid forms include an amorphous solid form, in which there is no long-range order in the positions of molecules (e.g., foams and glasses). These solid forms also include crystalline forms, in which constituent molecules are arranged in an orderly repeating pattern extending in all three spatial dimensions. The term "polymorph" refers to a particular crystalline form of a chemical compound that can exist in more than one crystal structure (e.g. lattice type) in the solid state. The term "packing polymorphs" refers to particular crystalline forms of a compound having different crystal packing. Crystalline forms of Compound 1 in this invention relate to embodiments which include a single polymorph (i.e. single crystalline form) and to embodiments which include a mixture of polymorphs (i.e. different crystalline forms). Polymorphs can differ in such chemical, physical and biological properties as crystal shape, density, hardness, color, chemical stability, melting point, hygroscopicity, suspensibility, solubility, dissolution rate and biological availability. One skilled in the art will appreciate that a polymorph of Compound 1 can exhibit beneficial effects (e.g., suitability for preparation of useful formulations, stability, improved biological performance) relative to another polymorph or a mixture of polymorphs of Compound 1. Differences with respect to chemical stability, filterability, solubility, hygroscopicity, melting point, solid density and flowability can have a significant effect on the development of production methods and formulations, and efficacy of plant disease control. Preparation and isolation of particular polymorphs of Compound 1 have now been achieved.

One crystalline polymorph form of Compound 1 is designated as polymorph Form A. This solid form is unsolvated. Polymorph Form A can be characterized by X-ray powder diffraction, single crystal X-ray structure analysis and Differential Scanning Calorimetry (DSC).

The powder X-ray diffraction pattern of polymorph Form A of Compound 1 is shown in FIG. 1A. The corresponding 2θ values are tabulated in Table 2 of Characterization Example 1. Polymorph Form A of Compound 1 can be identified by a room-temperature powder Cu(Kα1)-X-ray diffraction pattern having at least the 2θ reflection positions (in degrees)

| 2θ |
| --- |
| 6.395 |
| 12.668 |
| 14.507 |
| 14.99 |
| 18.984 |
| 22.23 |
| 23.885 |
| 24.919 |
| 26.34. |

Single crystal X-ray diffraction can also be used to characterize polymorph Form A. A description of single crystal X-ray diffraction of polymorph Form A is provided in Characterization Example 3. Crystals of polymorph Form A have a monoclinic unit cell and may exhibit a variety of morphologies with irregular plate morphology being most typical.

Polymorph Form A of Compound 1 can also be characterized by Differential Scanning Calorimetry (DSC). DSC indicates the melting point of polymorph Form A is about 168° C. The details of a DSC experiment are provided in Characterization Example 9. Polymorph Form A is physically and chemically stable in its pure solid form.

Pure Polymorph Form A can be prepared directly during the preparation of Compound 1 as described in Preparation Examples 1 and 2.

Another crystalline polymorph form of Compound 1 is designated as Polymorph Form B. This solid form is unsolvated. Polymorph Form B can be characterized by X-ray powder diffraction, single crystal X-ray structure analysis and Differential Scanning Calorimetry.

Figure 1B:
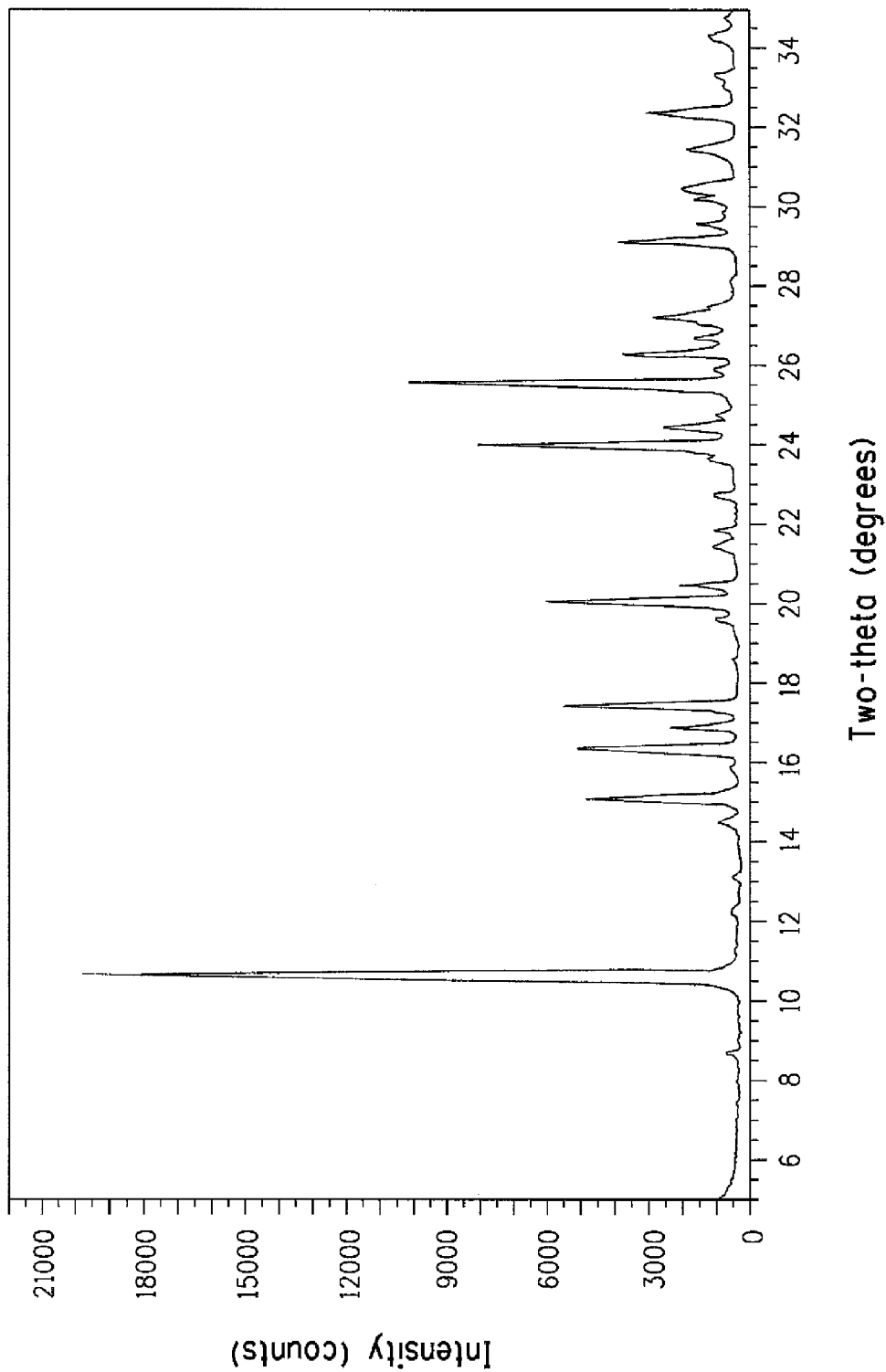
FIG. 1B shows room temperature Cu-K$\alpha$1 powder X-ray diffraction patterns of polymorph Form B of Compound 1 showing absolute X-ray intensity in counts graphed against 2$\theta$ reflection positions in degrees.

The powder X-ray diffraction pattern of polymorph Form B of Compound 1 is shown in FIG. 1B. The corresponding 2θ values are tabulated in Table 3 of Characterization Example 2. Polymorph Form B of Compound 1 can be identified by a room-temperature powder Cu(Kα1)-X-ray diffraction pattern having at least the 2θ reflection positions (in degrees)

| 2θ |
|---|
| 10.894 |
| 15.361 |
| 16.134 |
| 17.718 |
| 20.322 |
| 24.285 |
| 25.84 |
| 27.54 |
| 29.449. |

Single crystal X-ray diffraction can be used to characterize polymorph Form B. A description of single crystal X-ray diffraction of polymorph Form B is provided in Characterization Example 4. Crystals of polymorph Form B have an orthorhombic unit cell and may exhibit a variety of morphologies with prism morphology being most typical.

Polymorph Form B of Compound 1 can also be characterized by Differential Scanning Calorimetry. DSC indicates the melting point of polymorph Form B is about 143° C. The details of a DSC experiment are provided in Characterization Example 9.

Polymorph Form B can be prepared directly as described in Preparation Examples 4 and 5. Polymorph Form B can also be prepared from isolated polymorph Form A or mixtures of Forms A and B by forming a slurry of the polymorphs in a solvent with optional heating and then cooling back to room temperature or lower as described in Preparation Examples 3, 6, 7 and 8.

Compound 1 can also exist as an amorphous solid. The powder X-ray diffraction pattern (pXRD) for the amorphous form of Compound 1 shows a broad reflection pattern across the two-theta angle lacking distinct reflection signals and thus is readily distinguished from the pXRD patterns of crystalline forms of Compound 1. The amorphous solid form can be prepared by standard methods known in the art, such as evaporation to dryness of solutions containing Compound 1, by quick cooling of melted Compound 1, by spray drying a solution of Compound 1 or by freeze-drying a frozen solution containing Compound 1.

The preparation of polymorph Form A of Compound 1 can be accomplished by a process wherein Compound 1 is prepared from its starting materials as described in Preparation Examples 1 and 2. Preparation Examples 1 and 2 provide slightly different procedures for the preparation of the starting materials 1-(2-bromo-4-fluorophenyl)-2-propanone (compound of Formula 2) and 1-chloro-3-fluoro-2-isothiocyanatobenzene (compound of Formula 3). Preparation Examples 1 and 2 also provide a slightly different treatment of the initial condensation product salt (compound of Formula 4) that is either acidified to form a thioamide intermediate (compound of Formula 5) or alkylated to form an alkylated thioamide intermediate (compound of Formula 5a). Either intermediate can be reacted with methylhydrazine to form the compound of Formula 1 (4-(2-Bromo-4-fluorophenyl)-N-(2-chloro-6-fluorophenyl)-1,3-dimethyl-1H-pyrazol-5-amine, Compound 1).

An especially useful method to prepare Compound 1 is shown in Scheme 1 and exemplified in Preparation Examples 1 and 2. The method involves treating a compound of Formula 2 with a base in a solvent and then further contact with a compound of Formula 3 to form a salt of the initial condensation product (compound of Formula 4). The salt of Formula 4 can be neutralized with acid to form a thioamide intermediate of Formula 5 or it can be alkylated to form an alkylated thioamide intermediate of Formula 5a. Intermediates of Formula 5 or 5a are optionally isolated or immediately reacted in situ with methylhydrazine in the presence of a solvent to for the compound of Formula 1.

The starting ketone of Formula 2 can be prepared according to several procedures. One preparation starts from 2-bromo-4-fluorobenzeneacetonitrile as described in World Patent Publication WO 2012/031061 (Synthesis Example 7, Step A). The ketone of Formula 2 can also be prepared starting from 2-bromo-4-fluorobenzeneacetic acid as described in Preparation Example 1, Step A and 2-bromo-4-fluoroaniline as described in Preparation Example 2, Step A of the present specification. The starting isothiocyanate of Formula 3 can be prepared from 2-chloro-6-fluorobenzenamine (also called 2-chloro-6-fluoroaniline) using thiophosgene as described in Preparation Example 1, Step B. The starting isocyanate of Formula 3 can also be prepared using a multiple step procedure as described in Preparation Example 2, Step B.

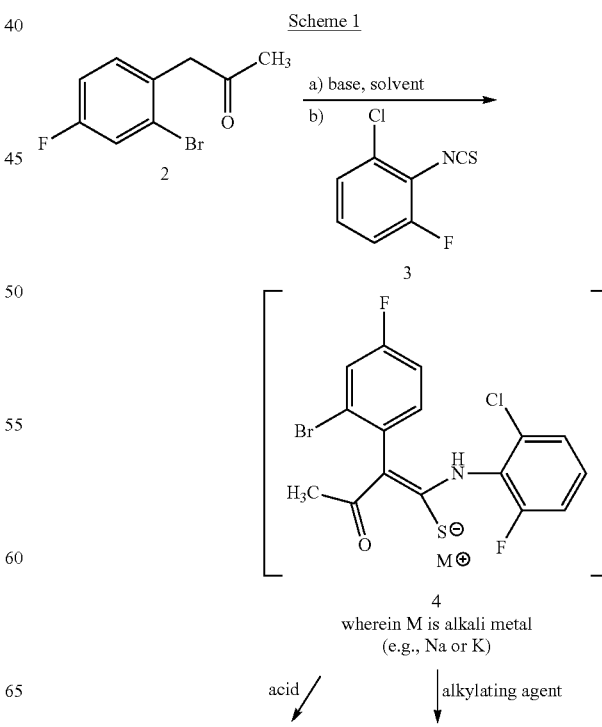

-continued

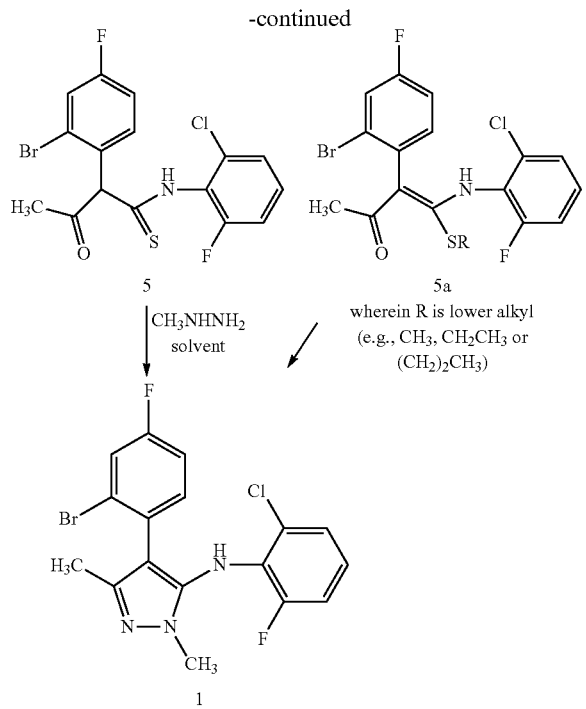

wherein R is lower alkyl (e.g., CH₃, CH₂CH₃ or (CH₂)₂CH₃)

The first step of Scheme 1 involves the condensation of the ketone of Formula 2 with the isothiocyanate of Formula 3, in the presence of a base, to give a salt of the initial condensation product (compound of Formula 4). Bases useful for the condensation reaction include hydrides, alkoxides, hydroxides or carbonates of sodium or potassium, such as sodium hydride, potassium tert-butoxide, sodium ethoxide, potassium hydroxide, sodium hydroxide or potassium carbonate. Amine bases (e.g., triethylamine or N,N-diisopropylethylamine) can also be used to effect the condensation. A particularly useful base is potassium hydroxide.

A variety of solvents are useful for the condensation and can be a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon or mixtures thereof. Useful solvents include tetrahydrofuran, methyl-tert-butylether, toluene, tert-butanol, ethanol, ethylacetate or mixtures thereof. Especially useful solvents are tetrahydrofuran and methyl-tert-butylether. Solvents are usually chosen for compatibility with the base selected for the reaction. The solvent used for the condensation step is referred to as the first solvent. Phase transfer catalysts can also be employed when the base has limited solubility in the solvent. For example in Preparation Example 2 Step C, tetrabutylammonium bromide is added to the mixture of potassium hydroxide in tetrahydrofuran. Tetrabutylammonium hydroxide is formed and acts as a soluble form of hydroxide base in the ether solvent. It is also important to minimize the amount of water in the reaction because water can lead to hydrolysis of the compound of Formula 3.

The condensation can be performed at a temperature ranging from a low of about −78° C. to a higher temperature of the boiling point of the solvent. A particularly useful temperature range is between −10° C. and 20° C. The condensation can be performed by either adding a mixture of the compounds of Formulae 2 and 3 to a cooled solution of the base in solvent or more preferably by first adding the ketone of Formula 2 to a cooled solution of the base in solvent and allowing it to react with the base for a period of time (1 hour or less) and then adding the isothiocyanate of Formula 3. The ratio of the base to the compound of Formula 2 is usually in the range of 1.0:1.0 to 1.5:1.0, with a slight excess preferred in the range of 1.1:1.0 to 1.3:1.0 depending on the solubility and reactivity of the base. The molar ratio of the compound of Formula 3 to the compound of Formula 2 can range from 0.9:1.0 to 1.2:1.0. A particularly useful molar ratio range of the compound of Formula 3 to the compound of Formula 2 is 0.95:1.00 to 1.10:1.00.

The initial condensation product is a salt of the thioamide intermediate (compound of Formula 4). The condensation product salt of Formula 4 is generally not isolated but instead treated in situ with either acid to give the intermediate thioamide of Formula 5 or treated with an alkylating agent to give the alkylated thioamide intermediate of Formula 5a. A variety of acids are useful for the neutralization of the salt of Formula 4 such as acetic acid, hydrochloric acid or citric acid. The amount of acid needed is that which will give a neutral or very slightly acidic pH. Acetic acid or citric acid is especially useful to carefully neutralize the reaction mixture to neutral pH. The reaction mixture containing the thioamide intermediate is treated with water and processed in the usual manner to isolate α-acetyl-2-bromo-N-(2-chloro-6-fluorophenyl)-4-fluorobenzene-ethanethioamide (compound of Formula 5) as a solid (described in Preparation Example 2, Step C). A variety of alkylating agents can be used to convert the salt of Formula 4 to the alkylated thioamide intermediate of Formula 5a wherein R is lower alkyl (e.g., methyl, ethyl or n-propyl). Compounds such as iodomethane, iodoethane, 1-bromopropane or dimethylsulfate are useful alkylating agents. A typical ratio of the alkylating agent to the compound of Formula 2 is 1.1:1.0 to 1.3:1.0. The reaction mixture containing the alkylated thioamide intermediate of Formula 5a is treated with aqueous acid and processed in the usual manner to isolate the intermediate as a solid. For example, when iodomethane is used as the alkylating agent, 3-(2-bromo-4-fluorophenyl)-4-[(2-chloro-6-fluorophenyl)amino]-4-(methylthio)-3-buten-2-one (compound of Formula 5a wherein R=methyl) is isolated (described in Preparation Example 1, Step C).

The second step of Scheme 1 involves the reaction of the intermediates of Formulae 5 or 5a with methylhydrazine. The intermediates can be isolated and purified before reacting with methylhydrazine in a solvent which may be different than that for the first step of Scheme 1. Alternatively the intermediates can be immediately reacted in situ with methylhydrazine in the original reaction mixture. An example of the methylated intermediate thioamide (Formula 5a wherein R=methyl) reacting with methylhydrazine without prior isolation can be found in World Patent Publication WO 2012/031061 (Synthesis Example 7, Step C). An example of the methylated intermediate thioamide (Formula 5a wherein R=methyl) reacting with methylhydrazine after first being isolated is described in Preparation Example 1, Step D. An example of the thioamide intermediate (Formula 5) reacting with methylhydrazine after first being isolated is described in Preparation Example 2, Step D.

The formation of the pyrazole ring in the second step of Scheme 1 requires reaction between the thioamide intermediate (or alkylated thioamide intermediate) and a buffered solution of methylhydrazine. The pH of the reaction medium affects the ratio of regioisomeric pyrazoles that can form from the reaction of methylhydrazine and the ketothioamide functional group of the intermediate 5 or 5a. The regioisomeric products of this reaction are 4-(2-bromo-4-fluorophenyl)-N-(2-chloro-6-fluorophenyl)-1,3-dimethyl-1H-pyrazol-5-amine (compound of Formula 1) and 4-(2-bromo-4- fluorophenyl)-N-(2-chloro-6-fluorophenyl)-1,5-dimethyl-1H-pyrazol-3-amine. In order to promote the maximum ratio (about 16:1 in favor of the compound of Formula 1) of pyrazole isomers a pH of 4 to 5 was found to be optimal. If the pH is too low then the reaction proceeds very slowly and if the pH is too high then regioselectivity is poor. This pH range can be obtained using a variety of buffering systems. Free base methylhydrazine can be combined with greater than one equivalent of acetic acid to produce a correctly buffered solution. The amount of acetic acid can be in the range of 1.1 to 2.5 equivalents, with a preferred ratio of free methylhydrazine to acetic acid of 1.0:2.0. Alternatively methylhydrazine sulfate can be used as the methylhydrazine source and treated with greater than one equivalent of triethylamine or sodium acetate. The amount of base (triethylamine or sodium acetate) can be in the range of 1.1 to 2.5 equivalents. The molar ratio of methylhydrazine to the thioamide intermediate 5 or 5a is typically in the range of 1.1:1.0 to 5.0:1.0. Particularly useful ratios of methylhydrazine to thioamide intermediate are in the range of 1.2:1.0 to 2.5:1.0.

A variety of solvents are useful for the pyrazole ring formation and can be water, a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon or mixtures thereof. Solvents are usually chosen for compatibility with the intermediate of Formula 5 or 5a and the methylhydrazine reagent. The methylhydrazine buffered solution usually needs to be polar in order to dissolve or partially dissolve the salts that make up the buffered solution. Solvents like methanol, ethanol or tetrahydrofuran/water mixtures are especially useful for the methylhydrazine solution. The intermediate of Formula 5 or 5a can be dissolved in the same solvent as the methylhydrazine or it can be in a different solvent. Particularly useful solvents for dissolving the thioamide intermediate are tetrahydrofuran, toluene and ethanol. Solvent can effect the regioselectivity of the reaction and a mixture of solvents (methylhydrazine solution in methanol and thioamide intermediate in toluene) has been found to provide a high level of regioselectivity. The solvent or solvents used for the pyrazole ring formation is referred to as the second solvent. The intermediate of Formula 5 or 5a can be added to the methylhydrazine solution or the methylhydrazine solution can be added to the intermediate thioamide. Either order of addition yields the desired pyrazole in good yield. The order of addition is usually determined by whether or not the intermediate thioamide is isolated.

The pyrazole formation can be performed at a temperature ranging from about 20° C. to the boiling point of the solvent. A particularly useful temperature range is between 40° C. and 75° C. The reaction is usually monitored by high pressure liquid chromatography to determine the duration of heating. The time needed to complete the reaction is somewhat dependent on the scale of the reaction. Typical time period needed to maximize the pyrazole formation (yielding the compound of Formula 1) is in the range of 3 to 18 hours Upon completion of the reaction, the reaction mixture is usually diluted with aqueous solutions to dissolve salts (triethylamine sulfate, sodium acetate etc.) and reduce the solubility of the product, thus promoting the crystallization of product of high purity. The reaction mixture can be treated with a variety of aqueous solutions like aqueous sodium or potassium carbonate, aqueous hydrochloric acid or neutral water. Another option is to exchange the reaction solvent for another as described in Preparation Example 2, Step D. Solvent exchange is sometimes desirable to replace a solvent with some water solubility or a high boiling point with a solvent with very little water solubility and/or a lower boiling point to facilitate the dissolution of salts in the aqueous phase and removal of the solvent from the product. The organic phase containing Compound 1 that results from the aqueous washes and the optional solvent exchange can be treated according to two different procedures.

The first option for treating the organic phase containing Compound 1 involves concentration of solvent to about 20-40% of its original volume. This reduces the volume of extraction solvent in which Compound 1 is soluble (e.g. toluene). The resultant slurry of Compound 1 is treated with seed crystals of polymorph Form B and optionally heated to 25-60° C. to facilitate crystallization to the desired polymorph Form B and conversion of any Form A to Form B. Crystallization time is determined by analyzing sample aliquots of the slurry by powder X-ray diffraction. When crystallization to polymorph Form B is complete, the slurry is diluted with another solvent (e.g. heptane) in which Compound 1 is less soluble to facilitate the filtration and recovery of polymorph Form B of Compound 1. This direct conversion process, without prior isolation of the solid polymorph Form A, is described in Preparation Example 4. Alternatively, the solvent containing the slurry of Compound 1 can be exchanged for the crystallization process. The original extraction solvent can be minimized and replaced with a third solvent to facilitate the crystallization to polymorph Form B. A variety of solvents are useful for the crystallization process and can be water, a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon or mixtures thereof. The solvent used for the crystallization process is referred to as the third solvent. The slurry in the third solvent is treated with seed crystals of polymorph Form B, optionally heated to 25-60° C. and monitored by powder X-ray diffraction analysis. When crystallization to polymorph Form B is complete, the slurry is diluted with another solvent (e.g. water) in which Compound 1 is less soluble to facilitate the filtration and recovery of polymorph Form B of Compound 1. This alternative direct conversion process, without prior isolation of the solid polymorph Form A, is described in Preparation Example 5.

The second option for treating the organic phase containing Compound 1 involves cooling the organic phase to a temperature in the range of 5 to 25° C. and filtering the product that precipitates out. The wet solid can be washed with water, to remove traces of salts and washed with an organic solvent like hexane or heptane to displace water and higher boiling solvents (e.g. toluene) to facilitate drying. The separated solid or wet cake of Compound 1 can then be further isolated by drying or removing the last traces of solvent adhering to the external surface of the solid in a vacuum oven. The isolated solid can be characterized by a variety of analytical methods. The preparation of Compound 1 according to this procedure usually yields polymorph Form A (as described in Preparation Examples 1 and 2) or a mixture of polymorph Form A and Form B wherein Form A predominates. To prepare a pure sample of polymorph Form B, the isolated solid product resulting from procedures such as Preparation Example 1 or 2 is subjected to a polymorph conversion process as described in Preparation Examples 3 and 6 through 8.

A variety of procedures can be used to prepare polymorph Form B of Compound 1. Selection of optimal procedures is typically based on a variety of factors, including the scale of the reaction. The temperature range for the conversion can range between 20° and the boiling point of the solvent. Performing the conversion at temperatures in the range of 20-30° C. provides mild conditions. The time needed for the conversion can vary depending on the reaction scale and solvent but usually can be accomplished between 1 and 18 hours. A variety of solvents can be used for the conversion process. Useful solvents include water, a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon and mixtures thereof. Particularly useful solvents include water, butyl acetate, methanol, 1-propanol or toluene. A mixture of methanol and water at ambient temperature is especially useful as described in Preparation Examples 3 and 5.

Seed crystals are usually used in the polymorph form conversion procedures. Seed crystals are used to promote conversion and/or increase the rate of conversion of polymorph Form A into polymorph Form B. The polymorph conversion reactions are often agitated by a variety of methods even if not explicitly stated. The form of agitation can be from shaking the reaction vessel or by stirring with a magnetic or mechanical stirrer. The polymorph conversion reactions can also be agitated by the boiling action of the solvent. Efficient agitation is not necessary for conversion of polymorph forms, but agitation can improve the efficiency of the process and shorten reaction times.

Polymorph Form B was first discovered as described in Preparation Example 9. It was isolated from an unstable formulation where polymorph Form A spontaneously converted into polymorph Form B. This was a source of seed crystals for some of the conversion experiments.

The relative stability of polymorph Forms A and B of Compound 1 were studied. The two polymorph forms were subjected to competitive interconversion experiments. Characterization Examples 6, 7 and 8 demonstrate that polymorph Form B is the more thermodynamically stable form at the temperatures used in the studies (20-50° C.). Characterization Example 5 describes the heating of a sample of polymorph Form B and the monitoring of its powder X-ray diffraction pattern. The analysis of the experiment indicates that polymorph Form B of Compound 1 heated from room temperature persists until about 138° C. where it converts to polymorph Form A. The newly-formed polymorph Form A persists until it melts at about 160°. The presence of a solid-solid transformation, below the melting point, upon heating of polymorph Form B indicates an enantiotropic relationship between polymorph Forms A and B, i.e. polymorph Form B is more stable below the transition temperature and polymorph Form A is more stable above the transition temperature. Characterization Example 9 describes differential scanning calorimetry experiments for polymorph Forms A and B. The analysis of the experiment shows an endothermic transition of polymorph Form B to Form A indicating an enantiotropic relationship between the two forms, i.e. polymorph Form B is thermodynamically more stable below the transition temperature (about 148° C.) and polymorph Form A is thermodynamically more stable above the transition temperature. The differences in transition temperature between the two experiments can be due to the rate of heating and other experimental variables. Characterization Examples 3 and 4 provide the calculated densities of the two crystal forms from their single crystal X-ray data. The density of polymorph Form B (1.673 g/cm$^3$) is greater than the density of polymorph Form A (1.604 g/cm$^3$) which is consistent with the density rule that states the most stable polymorph will have the highest density (R. Hilfiker (ed.), "Polymorphism in the Pharmaceutical Industry", 2006, page 33, Wiley-VCH, Weinheim, Germany).

Without further elaboration, it is believed that one skilled in the art using the preceding description can utilize the present invention. The following Examples are, therefore, to be construed as merely illustrative, and not limiting of the disclosure in any way whatsoever. The starting material for the following Examples may not have necessarily been prepared by a particular preparative run whose procedure is described in other Examples. Analytical methods used in the preparation examples are described below or in the Characterization Examples.

Proton-Nuclear Magnetic Resonance ($^1$H-NMR)

Proton-NMR analysis was performed on a Bruker Advance 300/400 instrument. The operational frequency was 400 MHz, spectral frequency range 0-16 ppm, delay time 2 seconds, pulse width of 12 μs, minimum number of scans was 8. Samples were prepared by weighing about 0.01 g of samples or reference standards, adding 0.6 mL of DMSO-d$_6$ to dissolve the contents and transferring into NMR tubes. Deuterated DMSO (DMSO-d$_6$) was from Cambridge Isotope Laboratory. $^1$H NMR spectra are reported in ppm downfield from tetramethylsilane; "s" means singlet, "d" means doublet, "t" means triplet, "m" means multiplet, "dd" means doublet of doublets and "br s" means broad singlet.

Preparation Example 1

Synthesis of Polymorph Form A of Compound 1 (Form A)

Step A: Preparation of 1-(2-bromo-4-fluorophenyl)-2-propanone

Acetic anhydride (950 mL, 10 mol) was degassed by bubbling nitrogen through it at room temperature. 2-Bromo-4-fluorobenzeneacetic acid (233 g, 1.0 mol) was dissolved in the acetic anhydride, cooled in an ice bath and treated dropwise with methyl imidazole (80 mL, 1.0 mol). The mixture was allowed to warm to room temperature over 18 hours. The reaction mixture was concentrated under vacuum and the resultant brown oil was added to a stirred ice/water mixture (500 mL) and allowed to warm to room temperature over 18 hours. Diethyl ether (400 mL) was added and the mixture was partitioned. The aqueous phase was extracted with diethyl ether and the combined organic phases were washed with water, saturated aqueous sodium bicarbonate solution and 1N hydrochloric acid. The ether solution was dried (MgSO$_4$), filtered and concentrated under vacuum to give a dark amber oil (228 g). The crude oil was dissolved in methanol (600 mL), treated dropwise with 1N aqueous sodium hydroxide (200 mL) and stirred at room temperature for 18 hours. The reaction mixture was concentrated under vacuum to remove most of the methanol, diluted with ice and treated with aqueous hydrochloric acid to acidify the mixture. The aqueous mixture was extracted with diethyl ether and the combined organic phases were dried (MgSO$_4$), filtered and concentrated under vacuum to give a dark amber oil (215 g). The crude oil was further purified by distillation under reduced pressure (6-7 mmHg), boiling 115 to 120° C. to yield the title product as a clear yellow oil (171 g).

$^1$H NMR (CDCl$_3$) δ 7.34-7.32 (dd, 1H), 7.20-7.17 (dd, 1H), 7.03-7.00 (td, 1H), 3.84 (s, 2H), 2.23 (s, 3H).

Step B: Preparation of 1-chloro-3-fluoro-2-isothiocyanatobenzene

A solution of 2-chloro-6-fluorobenzenamine (29.2 g, 0.20 mol) in chlorobenzene (200 mL) was treated with N,N- dimethylformamide (0.10 mL) and then thiophosgene (27.6 g, 0.24 mol) dropwise at room temperature. The reaction mixture was heated to reflux for 2.5 hours and allowed to stir at room temperature for 18 hours. The suspension was filtered through a pad of silica gel and washed with hexane. The filtrate was concentrated under vacuum to give a crude oil which was chromatographed on silica gel with hexane to yield the title compound as a light yellow oil (31.5 g).

$^1$H NMR (CDCl$_3$) δ 7.23-7.19 (m, 1H), 7.18-7.13 (td, 1H), 7.10-7.04 (m, 1H).

Step C: Preparation of 3-(2-bromo-4-fluorophenyl)-4-[(2-chloro-6-fluorophenyl)amino]-4-(methylthio)-3-buten-2-one To a solution of potassium tert-butoxide (23.5 g, 0.21 mol) in methyl tert-butyl ether (350 mL) at 0° C. was added a solution of 1-(2-bromo-4-fluorophenyl)-2-propanone (i.e. the product of Step A) (44.0 g, 0.19 mol) in methyl tert-butyl ether (70 mL) dropwise over 15 minutes at 10° C. The mixture was stirred for 1 h at 5-10° C. and then treated with a solution of 1-chloro-3-fluoro-2-isothiocyanatobenzene (i.e. the product of Step B) (32.0 g, 0.17 mol) in methyl tert-butyl ether (40 mL). The reaction mixture was stirred at 10° C. for 15 min and then the mixture was allowed to warm. After 30 minutes, when the temperature was 17° C., the suspension was treated with methyl iodide (15 mL, 0.24 mol) in methyl tert-butyl ether (15 mL) and continued to warm over 2 hours to room temperature. The resulting thin suspension was poured into a mixture of 1N hydrochloric acid (250 mL) and ice (200 g), partitioned and the aqueous phase extracted with methyl tert-butyl ether. The combined organic phases were washed with saturated aqueous NaCl solution, dried (MgSO$_4$), filtered and concentrated under vacuum to give a solid which was slurried in cold methanol (100 mL). The slurry was filtered and the filter cake rinsed with cold methanol (10° C.) and dried under vacuum to yield the title compound as a off-white solid (63.2 g).

$^1$H NMR (CDCl$_3$) δ 12.75 (s, 1H), 7.43-7.41 (dd, 1H), 7.34-7.32 (dd, 1H), 7.28-7.16 (m, 2H), 7.10-7.05 (m, 2H), 1.92 (s, 3H), 1.86 (s, 3H).

Step D: Preparation of 4-(2-Bromo-4-fluorophenyl)-N-(2-chloro-6-fluorophenyl)-1,3-dimethyl-1H-pyrazol-5-amine A solution of concentrated sulfuric acid (16 mL, 0.30 mol) in ethanol (500 mL) was treated with methylhydrazine (15 mL, 0.29 mol) in ethanol (50 mL) dropwise at room temperature. The reaction warmed and formed a white suspension. Triethylamine (63 mL, 0.45 mol) in ethanol (50 mL) was added dropwise while the mixture was at 30-35° C. The solids dissolved and the solution was treated with 3-(2-bromo-4-fluorophenyl)-4-[(2-chloro-6-fluorophenyl) amino]-4-(methylthio)-3-buten-2-one (i.e. the product of Step C) (63.2 g, 0.145 mol) and heated to 75° C. for 18 hours. The reaction mixture was cooled to 25-28° C. and treated with 1N sodium hydroxide solution (600 mL). The resultant slurry was cooled to 15° C. and treated with water (300 mL). The slurry was filtered, the solids washed with water and dried under vacuum to yield the title compound as a white solid (54.5 g). The melting point taken on an EZ-Melt apparatus (Standard Research System optical melting point) was 167.5-168.1° C.

$^1$H NMR (CDCl$_3$) δ 7.25-7.23 (dd, 1H), 7.06-7.03 (dd, 1H), 6.96-6.94 (dt, 1H), 6.89-6.85 (td, 1H), 6.79-6.75 (m, 1H), 6.70-6.66 (m, 1H), 5.46-5.43 (br.d, 1H), 3.80 (s, 3H), 2.10 (s, 3H).

Preparation Example 2

Synthesis of Polymorph Form A of Compound 1 (Form A)

Step A: Preparation of 1-(2-bromo-4-fluorophenyl)-2-propanone

Water (1 L) was treated with concentrated sulfuric acid (202 g, 98%) over 30 min and then the aqueous acid solution was cooled to 2° C. 2-Bromo-4-fluoroaniline (190 g, 1.0 mol) was added over 5 min and the solution was further cooled to 0° C. A solution of sodium nitrite (72.5 g, 1.05 mol) in water (110 mL) was added over 60 min, while maintaining the internal temperature below 5° C. The resultant diazonium salt slurry was treated with isopropenyl acetate (220 g, 2.2 mol) followed by copper sulfate pentahydrate (12.4 g, 0.05 mol) and stirred for 30 min during which time the copper sulfate dissolves. A solution of sodium sulfite (24 g, 0.2 mol) in water (80 mL) was added dropwise over 3 hours while maintaining the temperature between 10-20° C. After stirring the mixture for an additional 30 min at 20° C., hexanes (1 L) were added and the mixture was partitioned. The aqueous phase was extracted with hexanes (2×500 mL). The combined organic phases were washed with aqueous sodium hydroxide (0.5 N, 500 mL) and water (500 mL), and concentrated under reduced pressure to a brown oil (200 g).

The crude product can be purified by distillation under reduced pressure as in Preparation Example 1 or it can be purified via the bisulfite adduct as described below.

The crude 1-(2-bromo-4-fluorophenyl)-2-propanone (26.2 g, 0.11 mol) in heptane (104 mL) was treated with a solution of sodium metabisulfite (30 g, 0.16 mol) in water (52 mL). The mixture was stirred at 25° C. for 12 hours. The slurry was filtered and the filter cake washed with heptane (50 mL) and suction dried for 1 hour to give the bisulfite adduct as a pale yellow solid (39 g). The bisulfite adduct was treated with aqueous sodium hydroxide (10%, 104 mL) at 60° C. for 1 hour. The mixture was cooled to 25° C. and extracted with hexanes (2×100 mL). the combined organic phases was washed with water (20 mL) and concentrated under reduced pressure to give the title product (19.2 g) as a pale yellow oil.

$^1$H NMR (CDCl$_3$) δ 7.34-7.32 (dd, 1H), 7.20-7.17 (dd, 1H), 7.03-7.00 (td, 1H), 3.84 (s, 2H), 2.23 (s, 3H).

Step B: Preparation of 1-chloro-3-fluoro-2-isothiocyanatobenzene

A mixture of ammonium thiocyanate (38 g, 0.50 mol) and anhydrous acetone (200 mL) was heated to 45° C. Benzoyl chloride (64 g, 0.46 mol) was added over 1 hour while maintaining the temperature at 45-50° C. The mixture was heated for an additional hour at 45-50° C. and then cooled to ambient temperature. The slurry was filtered and the solids rinsed with anhydrous acetone (2×20 mL). The solids are discarded and the solution of benzoyl isothiocyanate is used immediately.

A solution of 2-chloro-6-fluoroaniline (50.0 g, 0.345 mol) in anhydrous acetone (80 mL) was cooled to 5° C. and treated with the benzoyl isothiocyanate solution at 5-10° C. over 1 hour. The mixture was warmed to 25-30° C. for 2 hours. Water (500 mL) was added over 1 hour with good stirring and the mixture allowed to stir for an additional hour at ambient temperature. The mixture was filtered and washed with water (2×100 mL) and the resultant N-[[(2- chloro-6-fluorophenyl)amino]thioxomethyl]benzamide was suction dried to give a solid (96 g).

$^1$H NMR (CDCl$_3$) δ 11.95 (s, 1H), 9.37 (s, 1H), 7.93 (m, 2H), 7.70 (m, 1H), 7.59 (m, 2H), 7.38 (m, 2H), 7.16 (m, 1H).

N-[[(2-chloro-6-fluorophenyl)amino]thioxomethyl]benzamide (96 g, 0.31 mol) was treated with an aqueous sodium hydroxide solution made from water (190 mL) and concentrated sodium hydroxide (32 g of 50%, 0.40 mol), and heated at 73-78° C. for 3 hours. The mixture was cooled to 10° C. and treated with concentrated hydrochloric acid (6 g of 36%, 0.06 mol) to a pH for about 7-9. After stirring for 30 min, the slurry was filtered and the filter cake was washed with cold (5° C.) water (2×100 mL) and dried in a vacuum oven at 70° C. to give the solid product (60 g) N-(2-chloro-6-fluorophenyl)thiourea.

$^1$H NMR (DMSO-d$_6$) δ 7.64 (s, 1H), 7.36 (m, 2H), 7.19 (m, 1H), 6.13 (s, 2H).

N-(2-chloro-6-fluorophenyl)thiourea (50.0 g, 0.245 mol) was dissolved in chlorobenzene (1.3 L) and the solution was heated up to 60° C. under vacuum to distill out about 20 mL of solvent to dry the reaction mixture. The vacuum was released and the mixture was heated rapidly (heated to reflux within 1 hour) to 125-135° C. with a slow subsurface sparge of nitrogen to remove released ammonia. The reaction was monitored by HPLC and when complete, the mixture was cooled to ambient temperature and the solvent distilled at reduced pressure (10 mmHg). When nearly all of the chlorobenzene was removed, the mixture was diluted with cyclohexane (150 mL) and filtered to remove a small quantity of insoluble material. The filtrate was concentrated to a crude liquid title product (1-chloro-3-fluoro-2-isothiocyanatobenzene) (40 g) and stored under nitrogen.

$^1$H NMR (CDCl$_3$) δ 7.23-7.19 (m, 1H), 7.18-7.13 (td, 1H), 7.10-7.04 (m, 1H).

Step C: Preparation of α-acetyl-2-bromo-N-(2-chloro-6-fluorophenyl)-4-fluorobenzeneethanethioamide A solution of potassium hydroxide (80 g of 86%, 1.23 mol) and tetrabutylammonium bromide (9.0 g, 0.028 mol) in tetrahydrofuran (1.38 L) was cooled to 10° C. under nitrogen. A solution of 1-(2-bromo-4-fluorophenyl)-2-propanone (i.e. the product of Step A) (230 g, 0.944 mol) in tetrahydrofuran (460 mL) was added over 1 hour at 10-15° C. Then a solution of 1-chloro-3-fluoro-2-isothiocyanatobenzene (i.e. the product of Step B) (201 g, 1.04 mol) in tetrahydrofuran (460 mL) was added over 1 hour and the mixture was stirred at 10-15° C. for 3 hours. The reaction mixture was further cooled to 0° C. and treated with acetic acid (100 g, 1.67 mol) over 30 min to bring the reaction mixture to about pH 7. Water (1.15 L) and toluene (1.4 L) were added and the phases were separated. The organic phase was washed with saturated aqueous sodium chloride (20 mL) and concentrated to about 250 mL volume at reduced pressure. The resultant slurry was treated with hexanes ((1.15 L) dropwise to crystallize the product. The slurry was cooled to 5-10° C., filtered and the collected solids washed with hexanes (400 mL). The solid title product (350 g) was dried in a vacuum oven. Melting Point 138-142° C.

$^1$H NMR (CDCl$_3$) δ 15.30 (s, 1H), 7.56 (m, 1H), 7.46 (m, 1H), 7.28 (m, 1H), 7.22 (m, 1H), 7.11 (m, 1H), 6.95 (m, 1H), 1.84 (s, 3H).

Step D: Preparation of 4-(2-Bromo-4-fluorophenyl)-N-(2-chloro-6-fluorophenyl)-1,3-dimethyl-1H-pyrazol-5-amine A solution of sodium acetate (41 g, 0.50 mol) in methanol (200 mL) was treated with methylhydrazine sulfate (36 g, 0.25 mol) at 25° C. under a nitrogen atmosphere. The mixture was heated to 60° C. for 30 min during which time a thin slurry formed. The mixture was cooled to ambient temperature, filtered and the insoluble solids were washed with methanol (50 mL). The filtrate was used as follows.

A solution of α-acetyl-2-bromo-N-(2-chloro-6-fluorophenyl)-4-fluorobenzene-ethanethioamide (i.e. the product of Step C) (63 g, 0.15 mol) in toluene (300 mL) was heated to 60° C. and treated with the methylhydrazine acetate solution. Hydrogen sulfide gas was evolved during the addition and was oxidized in a scrubber filled with bleach solution. The mixture was heated for 12 hours and then cooled to ambient temperature. Water (1 L) was added and the phases were separated. The aqueous phase was extracted with toluene and the combined organic phases were washed with hydrochloric acid (100 mL of 1N) and water (100 mL). The combined organic phases were concentrated under reduced pressure and the concentrated solution was diluted with heptane (300 mL) and cooled to 5° C. The resultant slurry was filtered and the solid dried under vacuum to isolate the title product (51 g). Melting point is 167-169° C.

$^1$H NMR (CDCl$_3$) δ 7.25 (m, 1H), 7.10 (m, 1H), 7.00 (m, 1H), 6.90 (m, 1H), 6.80 (m, 2H), 5.55 (br s, 1H), 3.89 (s, 3H), 2.17 (s, 3H).

Preparation Example 3

Conversion of Polymorph Form A to Form B of Compound 1 Using Water and Methanol Polymorph Form A of Compound 1 (100 g, 0.242 mol) was slurried in methanol (500 mL) and water (50 mL) at ambient temperature for 15 minutes. Seed crystals of polymorph Form B of Compound 1 (0.50 g, 1.21 mmol) were added. Additional water (50 mL) was added to the slurry and it was stirred at ambient temperature for 18 hours. The mixture was filtered and the filter cake was washed with methanol (50 mL) and suction dried for 3 hours. X-ray powder diffraction analysis identified the isolated solid as polymorph Form B of Compound 1.

The filtrate was combined with a second batch of polymorph Form A of Compound 1 (100 g, 0.242 mol), slurried at ambient temperature and seeded with polymorph Form B from the first batch. After stirring at ambient temperature for 18 hours, the mixture was filtered, washed and dried using the same procedure as batch 1 to give batch 2 solid. X-ray powder diffraction analysis identified the isolated solid from batch 2 as polymorph Form B of Compound 1.

The filtrate from batch 2 was combined with a third batch of polymorph Form A of Compound 1 (100 g, 0.242 mol) using the same procedure as for batch 2. X-ray powder diffraction analysis identified the isolated solid from batch 3 as polymorph Form B of Compound 1.

The filtrate from batch 3 was combined with a fourth batch of polymorph Form A of Compound 1 (109 g, 0.264 mol). Seed crystals of polymorph Form B from the first batch were added. The slurry was stirred at ambient temperature for 3 hours. The mixture was filtered and the filter cake was washed with a 9:1 mixture of methanol/water (200 mL) and suction dried for 3 hours. X-ray powder diffraction analysis identified the isolated solid from batch 4 as polymorph Form B of Compound 1. The four batches of polymorph Form B of Compound 1 were combined to give 395 grams (96.6% yield).

Preparation Example 4

Synthesis of Polymorph Form B of Compound 1 (Form B)

A solution of sodium acetate (6.01 g, 0.0732 mol) in methanol (30 mL) was treated with methylhydrazine sulfate (5.27 g, 0.0366 mol) at 25° C. under a nitrogen atmosphere. The mixture was heated to 54° C. for 45 min during which time a thick slurry formed. The mixture was cooled to ambient temperature, filtered through Celite and the insoluble solids were washed with methanol (20 mL). The filtrate was used as follows.

A solution of α-acetyl-2-bromo-N-(2-chloro-6-fluorophenyl)-4-fluorobenzene-ethanethioamide (i.e. the product of Preparation Example 2, Step C) (10.0 g, 0.0229 mol) in toluene (50 mL) was heated to 60° C. and treated with the methylhydrazine acetate solution over 30 minutes. Hydrogen sulfide gas was evolved during the addition and was oxidized in a scrubber filled with bleach solution. The mixture was heated for 7 hours and then cooled to 35° C. Water (150 mL) was added and the phases were separated. The aqueous phase was extracted with toluene (50 mL) and the combined organic phases were washed with hydrochloric acid (50 mL of 0.1N) and water (50 mL). The combined organic phases were dried with sodium sulfate, filtered and concentrated under reduced pressure to 30% of its original volume.

The resultant slurry was heated to 50° C. and treated with polymorph Form B seed crystals. The stirring was continued for 5 hours and then the slurry was cooled to 30° C., treated with heptane (50 mL) and concentrated under vacuum. The resultant thick slurry was diluted with heptane (90 mL), cooled to 5° C., stirred for 30 min, filtered and the collected solid was dried in a vacuum oven at 50° C. for 12 hours to give 4-(2-Bromo-4-fluorophenyl)-N-(2-chloro-6-fluorophenyl)-1,3-dimethyl-1H-pyrazol-5-amine (7.6 g). The product was confirmed to be polymorph Form B by X-ray powder diffraction analysis.

Preparation Example 5

Synthesis of Polymorph Form B of Compound 1 (Form B)

A procedure identical to the first two paragraphs of Preparation Example 4 was used to generate a slurry of the Compound 1 in toluene. The slurry was diluted with methanol (50 mL) and concentrated to reduce the amount of toluene present. The mixture was diluted with methanol (40 mL), stirred at 25° C. for 15 min, treated with polymorph Form B seed crystals and stirred for 1 hour. The slurry was further treated with water (10 mL), stirred for 16 hours at 25-27° C., filtered and dried in a vacuum oven at 50° C. for 6 hours to give 4-(2-Bromo-4-fluorophenyl)-N-(2-chloro-6-fluorophenyl)-1,3-dimethyl-1H-pyrazol-5-amine (7.7 g). The product was confirmed to be polymorph Form B by X-ray powder diffraction analysis.

Preparation Example 6

Preparation of Polymorph Form B of Compound 1 (Suspension in Toluene)

To a 250 mL 4-neck roundbottom flask fitted with a thermocouple, a cold water reflux condenser and a nitrogen inlet was added 4.55 g of Compound 1, polymorph Form A (confirmed by pXRD). Toluene (15 g) was added and the resulting slurry was stirred under nitrogen. The mixture was seeded with 0.24 g of polymorph Form B of Compound 1 (confirmed by pXRD). The mixture was heated in the range of 43 to 48° C. and approximately 2 g of toluene was added to improve mixing. The slurry was stirred for 16.5 hours. The heat source was removed and the reactor contents were allowed to cool to room temperature over six hours. The slurry was filtered on filter paper in a Büchner funnel under vacuum. The filter cake was transferred to a drying dish and placed in a vacuum oven at 60° C. to dry under vacuum (approximately 18-28 in Hg) overnight. A white solid (4.6 g) was obtained after drying, and pXRD analysis indicated a match to polymorph From B.

Preparation Example 7

Preparation of Polymorph Form B of Compound 1 (Suspension in Toluene)

To a 250 mL 4-neck roundbottom flask fitted with a thermocouple, a cold water reflux condenser and a nitrogen inlet was added 20.7 g of Compound 1, polymorph Form A (confirmed by pXRD). Toluene (85.1 g) was added and the resulting slurry was stirred under nitrogen. The mixture was seeded with 0.92 g of a sample of Compound 1 known to be a mixture of both polymorph Form A and polymorph Form B. The mixture was heated to 48° C. for 15 hours. The heat source was removed and the reactor contents were cooled to 22° C. over 2.5 hours. The slurry was filtered on a coarse glass fritted funnel under vacuum. The filter cake was transferred to a drying dish and placed in a vacuum oven at 60° C. to dry under vacuum (approximately 18-28 in Hg) overnight. A white solid (18.8 g) was obtained and the pXRD analysis indicated a match to polymorph Form B.

Preparation Example 8

Preparation of Polymorph Form B of Compound 1 (Suspension in Toluene and n-Heptane)

To a 250 mL 4-neck roundbottom flask fitted with a thermocouple, a cold water reflux condenser, addition funnel and a nitrogen inlet were added 12.7 g of Compound 1, polymorph Form A (confirmed by pXRD). The toluene filtrate from Example 5 (60.0 g) was added and the resulting slurry was stirred under nitrogen. The mixture was seeded with 0.27 g of a sample of Compound 1 known to be a mixture of polymorph Form A and polymorph Form B. The mixture was heated to 51° C. and for 15 hours. The heat source was removed and the reactor contents were cooled to 20° C. over 3.75 hours. N-heptane (12 g) was added to the slurry dropwise via the addition funnel over 7 minutes. The slurry was stirred for 45 minutes. The resultant slurry was filtered on a coarse glass fritted funnel under vacuum. The filter cake (15.0 g) was transferred to a drying dish and placed in a vacuum oven at 50° C. to dry under vacuum (approximately 18-28 in Hg) overnight. A white solid (14.0 g) was obtained and the pXRD analysis indicated a match to polymorph Form B.

Preparation Example 9

Stability of Crystal Forms A and B in a Liquid Formulation

The polymorph Form A of Compound 1 was prepared as described in Preparation Example 1. The presence of polymorph Form A was confirmed by pXRD. Polymorph Form A of Compound 1 (50 grams) was added to a 1 quart boston round bottle. The additional formulation ingredients were weighed into the bottle in the order shown in Table 1.

TABLE 1

| Ingredient | Function | Weight (%) | Weight (grams) |
|---|---|---|---|
| polymorph Form A of Compound 1 | fungicide technical | 7.57 | 48.5 |
| $C_8$-$C_{10}$ fatty acid dimethylamide | primary solvent | 62.13 | 398.0 g |
| 2-ethylhexyl-S-lactate | Co-solvent | 15.3 | 98.03 |
| ethoxylated caster oil (POE30) | nonionic surfactant | 7 | 44.85 |
| ethoxylated propoxylated tristyryphenol (block copolymer) | nonionic surfactant | 3 | 19.22 |
| 60% calcium dodecyl benzene sulfonate in 2-ethylhexanol | anionic surfactant | 5 | 32.03 |
| | total | 100 | 640.69 |

The bottle was capped and the contents were magnetically stirred at 20° C. for 18 hours. The technical was fully dissolved in the formulation ingredients. The resultant 7EC (emulsifiable concentrate, nominally 70 grams active/liter) formulation was stored at ambient temperature for 35 days. The sample showed visible signs of white solids precipitating from solution. The sample was held at ambient temperature for an additional 6 months. The formulation sample was then filtered and the white solids collected. The solids were washed with water and dried in an oven (54° C.) for 1 hour. The recovered solids gave a proton NMR consistent with Compound 1, however the powder X-ray diffraction spectrum was different from that of polymorph Form A of Compound 1. This was the first appearance of polymorph Form B of Compound 1.

The precipitation of solids of the technical fungicide constitute an undesirable formulation instability which may result in undesired effects such as not providing the full extent of bioefficacy or clogging of application equipment.

Characterization Example 1

X-Ray Powder Diffraction for Compound 1 Polymorph Form A

Powder X-ray diffraction was used to identify the crystalline phases of various samples of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu-K(alpha1) ($\lambda$=1.54059 Å) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 is used with the International Committee for Diffraction Data database PDF4+ 2008 for phase identification. Diffraction maxima for Form A of Compound 1 were calculated using the MDI/Jade "Find Peaks" routine and are listed Table 2.

TABLE 2

2θ X-ray Maxima (in degrees) for Polymorph Form A of Compound 1

| 2θ | 2θ | 2θ | 2θ | 2θ | 2θ | 2θ |
|---|---|---|---|---|---|---|
| 6.395 | 17.067 | 23.885 | 29.949 | 34.329 | 37.419 | 40.209 |
| 12.035 | 18.984 | 24.919 | 30.834 | 34.563 | 37.938 | 40.577 |
| 12.668 | 19.524 | 25.352 | 31.153 | 35.23 | 38.357 | 40.997 |
| 13.122 | 20.573 | 26.34 | 31.956 | 35.636 | 38.651 | |
| 14.145 | 21.194 | 27.894 | 32.256 | 36.134 | 39.023 | |
| 14.507 | 22.23 | 28.445 | 32.508 | 36.385 | 39.224 | |
| 14.99 | 23.215 | 29.146 | 33.894 | 36.836 | 39.74 | |

Characterization Example 2

X-Ray Powder Diffraction Pattern for Compound 1 Polymorph Form B

Powder X-ray diffraction was used to identify the crystalline phases of various samples of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu-K(alpha1) ($\lambda$=1.54059 Å) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 is used with the International Committee for Diffraction Data database PDF4+ 2008 for phase identification. Diffraction maxima for Form B of Compound 1 were calculated using the MDI/Jade "Find Peaks" routine and are listed Table 3.

TABLE 3

2θ X-ray Maxima (in degrees) for Polymorph Form B of Compound 1

| 2θ | 2θ | 2θ | 2θ | 2θ | 2θ | 2θ |
|---|---|---|---|---|---|---|
| 8.926 | 19.938 | 25.84 | 30.784 | 35.654 | 40.061 | 44.691 |
| 10.894 | 20.322 | 26.607 | 31.439 | 36.248 | 40.52 | 44.954 |
| 13.371 | 20.771 | 26.977 | 31.754 | 36.798 | 40.663 | 45.375 |
| 14.741 | 21.694 | 27.328 | 32.659 | 37.085 | 41.148 | 46.109 |
| 15.361 | 23.046 | 27.54 | 33.364 | 37.367 | 41.514 | 46.897 |
| 16.134 | 23.951 | 28.394 | 33.593 | 37.897 | 42.734 | 47.495 |
| 16.599 | 24.285 | 29.449 | 34.527 | 38.676 | 43.021 | 48.167 |
| 17.199 | 24.737 | 29.85 | 35.097 | 38.956 | 43.334 | 48.632 |
| 17.718 | 25.051 | 30.467 | 35.4 | 39.611 | 43.632 | 49.05 |

Characterization Example 3

Single Crystal X-Ray Diffraction for Polymorph Form a of Compound 1

Suitable single crystals for polymorph Form A were grown from methanol evaporation. A colorless irregular plate with approximate dimensions of 0.520×0.300×0.060 mm was chosen for data collection and mounted on a polymer loop. Single crystal data was collected using a Bruker Platform goniometer with an Apex-II detector. The diffractometer was equipped with an incident beam monochromator using Mo-Kα radiation ($\lambda$=0.71073 Å) and a monocap collimator. The crystals were cooled in a −100° C. nitrogen flow during data collection.

The data were indexed and integrated using the Apex-II suite of programs including Sainplus and SADABS. The monoclinic cell parameters were determined to be: a=7.870(5) Å, b=28.037(16) Å, c=7.976(5) Å, beta=103.875(10) °, volume=1708.6(17) Å$^3$. The space group was determined to be P21/n. The molecular weight was 412.66 g/mol giving a calculated density of 1.604 g/cm$^3$, and μ(Mo)=2.59 mm$^{-1}$ for Z=4. Data reduction led to 3487 unique data from a two-theta range=5.46 to 52.92°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=15.57, goodness-of-fit on F$^2$=1.06, R indices[I>4sigma(I)] R1=0.0564, wR2=0.1222, R indices (all data) R1=0.0940, wR2=0.1365, max difference peak and hole=0.876 and −0.720 e/Å$^3$. The asymmetric unit contains one molecule. The atomic fractional coordinates (×10$^4$) and equivalent isotropic displacement parameters are listed in Tables 4 and 5. U(eq) is defined as one third of the trace of the orthogonalized Uij tensor. The estimated standard deviations are shown in parentheses.

TABLE 4

Atomic Coordinates (×10$^4$) and Equivalent Isotropic Displacement Parameters (A$^2$ × 10$^3$) for Compound 1 Polymorph Form A

| Atom | x | y | z | U(eq) |
|---|---|---|---|---|
| Cl(1) | 2072(6) | 1557(2) | −654(6) | 58(1) |
| F(1) | −4289(13) | 1130(5) | −2620(16) | 58(1) |
| Cl(1') | −4627(5) | 1168(2) | −2568(7) | 58(1) |
| F(1') | 1813(14) | 1468(4) | −509(14) | 58(1) |
| Br(1) | 1696(1) | 1042(1) | 4113(1) | 73(1) |
| F(2) | −4128(5) | 158(1) | 3495(5) | 100(1) |
| N(1) | −1612(4) | 1819(1) | −1237(4) | 34(1) |
| N(2) | 287(5) | 2573(1) | 2306(4) | 43(1) |
| N(3) | −240(4) | 2454(1) | 603(4) | 38(1) |
| C(1) | −982(5) | 2016(1) | 407(5) | 32(1) |
| C(2) | −926(5) | 1836(1) | 2036(5) | 32(1) |
| C(3) | −115(5) | 2203(2) | 3167(5) | 40(1) |
| C(4) | 244(7) | 2211(2) | 5099(6) | 58(1) |
| C(5) | 28(6) | 2778(2) | −726(6) | 51(1) |
| C(6) | −1267(6) | 1334(2) | −1456(5) | 38(1) |
| C(7) | 442(6) | 1166(2) | −1110(6) | 53(1) |
| C(8) | 853(10) | 687(2) | −1251(8) | 76(2) |
| C(9) | −482(13) | 377(2) | −1772(8) | 92(2) |
| C(10) | −2187(12) | 518(2) | −2198(7) | 86(2) |
| C(11) | −2564(6) | 997(2) | −2047(6) | 58(1) |
| C(12) | −1704(5) | 1390(1) | 2436(5) | 32(1) |
| C(13) | −766(5) | 1015(2) | 3354(5) | 41(1) |
| C(14) | −1575(7) | 597(2) | 3712(6) | 56(1) |
| C(15) | −3332(7) | 564(2) | 3126(7) | 58(1) |
| C(16) | −4350(6) | 914(2) | 2189(6) | 52(1) |
| C(17) | −3540(5) | 1324(2) | 1855(5) | 41(1) |

TABLE 5

Hydrogen Coordinates (×10$^4$) and Isotropic Displacement Parameters (A$^2$ × 10$^3$) for Compound 1 Polymorph Form A

| Atom | x | y | z | U(eq) |
|---|---|---|---|---|
| H(4A) | 313 | 2542 | 5501 | 86 |
| H(4B) | 1357 | 2050 | 5590 | 86 |
| H(4C) | −703 | 2047 | 5470 | 86 |
| H(5A) | −1090 | 2835 | −1558 | 76 |
| H(5B) | 860 | 2637 | −1322 | 76 |
| H(5C) | 495 | 3081 | −196 | 76 |
| H(8A) | 2035 | 582 | −989 | 92 |
| H(9A) | −222 | 47 | −1843 | 111 |
| H(10A) | −3099 | 293 | −2591 | 103 |

TABLE 5-continued

Hydrogen Coordinates (×10$^4$) and Isotropic Displacement Parameters (A$^2$ × 10$^3$) for Compound 1 Polymorph Form A

| Atom | x | y | z | U(eq) |
|---|---|---|---|---|
| H(14A) | −913 | 345 | 4348 | 67 |
| H(16A) | −5579 | 873 | 1783 | 62 |
| H(17A) | −4227 | 1572 | 1217 | 49 |
| H(1) | −2550(60) | 1941(17) | −1720(60) | 47(14) |

Characterization Example 4

Single Crystal X-Ray Diffraction for Polymorph Form B of Compound 1

Suitable single crystals of polymorph Form B of Compound 1 were grown from acetonitrile. A colorless prism with approximate dimensions of 0.480×0.260×0.260 mm was chosen for data collection and mounted on a polymer loop. Single crystal data was collected using a Bruker Platform goniometer with an Apex-II detector. The diffractometer is equipped with an incident beam monochromator using Mo-Kα radiation (λ=0.71073 Å) and a monocap collimator. The crystals were cooled in a −100° C. nitrogen flow during data collection.

The data were indexed and integrated using the Apex-II suite of programs including Sainplus and SADABS. The orthorhombic cell parameters were determined to be: a=14.285(3) Å, b=11.464(2) Å, c=20.010(3) Å, volume=3276.9(10) Å$^3$. The space group was determined to be Pbca. The molecular weight was 412.66 g/mol giving a calculated density of 1.673 g/cm$^3$, and μ(Mo)=2.70 mm$^{-1}$ for Z=8. Data reduction led to 3730 unique data from a two-theta range=4.98 to 55.04°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=16.73, goodness-of-fit on F$^2$=1.04, R indices[I>4sigma(I)] R1=0.0444, wR2=0.0902, R indices (all data) R1=0.0890, wR2=0.1067, max difference peak and hole=0.538 and −0.466 e/Å$^3$. The asymmetric unit contains one molecule. The atomic fractional coordinates (×10$^4$) and equivalent isotropic displacement parameters are listed in Tables 6 and 7. U(eq) is defined as one third of the trace of the orthogonalized Uij tensor. The estimated standard deviations are shown in parentheses.

TABLE 6

Atomic Coordinates (×10$^4$) and Equivalent Isotropic Displacement Parameters (A$^2$ × 10$^3$) for Compound 1 Polymorph Form B

| Atom | x | y | z | U(eq) |
|---|---|---|---|---|
| Br(1) | 451(1) | 1562(1) | 1480(1) | 43(1) |
| Cl(1) | 4288(1) | 1193(1) | −365(1) | 40(1) |
| F(1) | 4638(1) | 3504(2) | 1767(1) | 39(1) |
| F(2) | 1994(2) | −236(2) | 3569(1) | 47(1) |
| N(1) | 3521(2) | 2304(2) | 861(2) | 24(1) |
| N(2) | 2142(2) | 4872(2) | 1000(1) | 24(1) |
| N(3) | 2840(2) | 4194(2) | 734(1) | 23(1) |
| C(1) | 2923(2) | 3174(3) | 1074(2) | 21(1) |
| C(2) | 2257(2) | 3179(3) | 1572(2) | 22(1) |
| C(3) | 1785(2) | 4250(3) | 1497(2) | 23(1) |
| C(4) | 966(2) | 4681(3) | 1882(2) | 30(1) |
| C(5) | 3326(3) | 4570(3) | 137(2) | 33(1) |
| C(6) | 4487(2) | 2427(3) | 770(2) | 23(1) |
| C(7) | 4948(2) | 1923(3) | 229(2) | 25(1) |

TABLE 6-continued

Atomic Coordinates (×10⁴) and Equivalent Isotropic Displacement Parameters (A² × 10³) for Compound 1 Polymorph Form B

| Atom | x | y | z | U(eq) |
|---|---|---|---|---|
| C(8) | 5908(3) | 2010(3) | 147(2) | 31(1) |
| C(9) | 6431(2) | 2629(3) | 601(2) | 34(1) |
| C(10) | 6003(2) | 3148(3) | 1139(2) | 31(1) |
| C(11) | 5052(3) | 3023(3) | 1218(2) | 26(1) |
| C(12) | 2155(2) | 2280(3) | 2098(2) | 23(1) |
| C(13) | 1417(2) | 1498(3) | 2134(2) | 27(1) |
| C(14) | 1352(3) | 646(3) | 2621(2) | 33(1) |
| C(15) | 2047(3) | 600(3) | 3086(2) | 32(1) |
| C(16) | 2788(3) | 1348(3) | 3094(2) | 34(1) |
| C(17) | 2840(2) | 2190(3) | 2597(2) | 30(1) |

TABLE 7

Hydrogen Coordinates (×10⁴) and Isotropic Displacement Parameters (A² × 10³) for Compound 1 Polymorph Form B

| Atom | x | y | z | U(eq) |
|---|---|---|---|---|
| H(4A) | 917 | 5529 | 1832 | 44 |
| H(4B) | 1047 | 4487 | 2356 | 44 |
| H(4C) | 394 | 4312 | 1714 | 44 |
| H(5A) | 3559 | 3886 | −106 | 49 |
| H(5B) | 3854 | 5070 | 262 | 49 |
| H(5C) | 2895 | 5008 | −150 | 49 |
| H(8A) | 6204 | 1642 | −222 | 38 |
| H(9A) | 7088 | 2698 | 543 | 40 |
| H(10A) | 6358 | 3588 | 1451 | 37 |
| H(14A) | 843 | 113 | 2631 | 40 |
| H(16A) | 3257 | 1295 | 3429 | 40 |
| H(17A) | 3352 | 2717 | 2594 | 35 |
| H(1) | 3360(20) | 1700(30) | 843(15) | 10(9) |

Characterization Example 5

Temperature-Dependent X-Ray Powder Diffraction for Polymorph Form B of Compound 1

To assess the stability of polymorph Form B of Compound 1 with respect to temperature, X-ray powder diffraction patterns were obtained while heating a sample of Form B from 25° C. to above its melting point. The measurement was conducted at the 5-IDD beam line at the Advanced Photon Source synchrotron located at the Argonne National Laboratory (Argonne, Ill., USA). A Differential-Scanning Calorimeter (DSC, Model DSC600, Linkam Scientific Instruments, Tadworth, U.K.) was mounted in vertical orientation to allow insertion of the DSC into the X-ray beam. The DSC was positioned in the beam line to accept a 100-200 µm square beam under high vacuum. The standard quartz window was replaced with polyimide film (Kapton®, 8 µm thickness, DuPont, Wilmington, Del., USA). An internal thermocouple was installed for temperature recording. A circular charged couple device (CCD) detector (Model Mar165, 165 mm diameter, Marresearch GmbH, Norderstedt, Germany) was used to detect the X-rays scattered from the sample. The detector was equipped with an aluminum cone that covered the detector and extended 100 mm from the face of the detector. This cone was equipped with a beam stop support and 5×3 mm lead beam stop. The cone was continuously purged with helium to minimize air scattering.

A sample (~20 mg) of polymorph Form B of Compound 1 was loaded in low-mass aluminum pans with hermetically sealed lids (Model Tzero, TA Instruments, New Castle, Del., USA). A 5 mm pin punch was used to tamp the sample into place. The sample was slowly compressed using this pin punch to about 0.5 mm below the top of the pan. The lid was securely installed using a Tzero press with the appropriate mandrels. A small spring (3-4 coils of 215 µm think stainless steel wire, 7 mm coil diameter) was utilized to mount and center the sample pan into the DSC.

The run parameters during the data collection were as follows. The temperature was increased linearly from 25° C. to 215° C. at a rate of 10° C. per minute, then decreased linearly from 215° C. to 25° C. at a rate of 20° C. per minute. The temperature was controlled using the Linkam CI93 temperature controller and LNP cooling pump. The data was collected using Linkam Linksys32 software. The X-ray data was collected simultaneously, but independently. The wavelength was tuned to 0.07293 nm. The CCD detector was set at high resolution, 79 µm pixel size. The distance between sample and CCD detector was 115 mm. Exposure time was 0.1 seconds, the frame rate was 1 frame per 10 seconds. The X-ray system was controlled using Certified Scientific Software SPEC and APS EPICS. The data reduction was performed using macros written to work with the SPEC software to reduce the two-dimensional patterns from the detector to a standard one-dimensional pXRD pattern relating scattered X-ray intensity to the scattering angle. The one-dimensional pXRD files were converted to Jade® format to allow further analysis using MDI/Jade software version 9.1. For crystal form identification, the pXRD patterns of the test sample were compared to the single-crystal reference patterns of Forms A and B, respectively.

The analysis of the pXRD patterns of the test sample indicates that polymorph Form B of Compound 1 heated from room temperature persists until 138° C. where it converts to polymorph Form A. The newly-formed polymorph Form A persists until it melts at 160° C. and above this temperature there is no structure to the sample.

The presence of a solid-solid transformation, below the melting point, upon heating of polymorph Form B indicates an enantiotropic relationship between polymorph Forms A and B, i.e. polymorph Form B is more stable below the transition temperature and polymorph Form A is more stable above the transition temperature.

Characterization Example 6

Relative Stability of Polymorph Forms A and B of Compound 1 at Elevated Temperature Form-conversion experiments were conducted using several organic solvents and a sample of Compound 1 known to be a mixture of both polymorph Form A and polymorph Form B.

In each experiment, about 0.5 g of Compound 1 was dispersed in 5 to 10 mL of the solvent in a the glass screw cap vial with magnetic stir bar. The mixture was then stirred at 50° C. for approximately 100 hours. The mixture was allowed to cool to 20° C. and then filtered on filter paper in a Büchner funnel under vacuum. The filtered solids were dried in a vacuum oven at 50-60° C. for about 18 hours and analyzed by pXRD. Table 8 below shows the obtained polymorph form by solvent type.

TABLE 8

Polymorph form obtained by mixing Form B of Compound 1
in various solvents

| Solvent | Resulting Polymorph Form |
| --- | --- |
| 1-propanol | B |
| Toluene | B |
| Methyl cyclohexane | B |
| n-Butyl acetate | B |

Characterization Example 7

Relative Stability of Polymorph Forms A and B of Compound 1 at Elevated Temperature Form-conversion experiments were conducted using several organic solvents and a sample of Compound 1 known to be a mixture of both polymorph Form A and polymorph Form B.

In each experiment, about 0.7 g of Compound 1 was dispersed in 1 to 4 mL of the solvent in a the glass screw cap vial with magnetic stir bar. The mixture was then stirred at 50° C. for approximately 7 days. The mixture was allowed to cool slowly to 20° C. and then filtered on filter paper in a Büchner funnel under vacuum. Residual solvent in the filtered solids was allowed to evaporate at room temperature over several days. The solids were analyzed by pXRD. Table 9 below shows the obtained polymorph form by solvent type.

TABLE 9

Polymorph form obtained by mixing Form B of Compound 1
in various solvents

| Solvent | Resulting Polymorph Form |
| --- | --- |
| Tetrahydrofuran | B |
| Ethyl acetate | B |
| Acetonitrile | B |

Characterization Example 8

Relative Stability of Polymorph Forms A and B of Compound 1

Form-conversion experiments were conducted using a range of solvents and a sample of Compound 1 known to be a mixture of both polymorph Form A and polymorph Form B.

In each experiment, about 0.6 to 0.8 g of Compound 1 was dispersed in 4 to 10 mL of the solvent in a the glass screw cap vial with magnetic stir bar. The mixture was then stirred at 20° C. for approximately 7 days. The stir bar was removed and the solvent was slowly removed by flowing nitrogen oven the uncapped vial for 17 days. The solids were analyzed by pXRD. Table 10 below shows the obtained polymorph form by solvent type.

TABLE 10

Polymorph form obtained by mixing Form B of Compound 1
in various solvents

| Solvent | Resulting Polymorph Form |
| --- | --- |
| 1-propanol | B |
| Toluene | B |
| n-Butyl acetate | B |

Characterization Example 9

Differential Scanning Calorimetry Experiments

Differential Scanning Calorimetry was used to study the crystalline phases of various samples of Compound 1. Data were obtained with a TA Instruments Q20-1220 Differential Scanning Calorimeter (V24.2 Build 107) using a standard cell (FC-03859). Samples were prepared by weighing between 4 and 5 mg of Compound 1 in a gold plated pan (Fauske and Associates, LLC, Burr Ridge, Ill.; part number DSC-M20). The corresponding lid was crimped tightly to the pan and the assembled crucible was inserted into the calorimeter. An empty crucible of the same type was prepared the same way and inserted as the reference. After the instrument was initialized, the sample was first equilibrated at 25° C. and then heated at 2° C./min to a maximum temperature of 225° C.

The DSC thermogram for polymorph Form A of Compound 1 was observed to exhibit a sharp melting endotherm with a signal maximum at about 168° C. and a heat of fusion of 78 J/g.

The DSC thermogram for polymorph Form B of Compound 1 was observed to exhibit a broad endotherm with a signal maximum at about 148° C. and a heat of transition of 12 J/g, and a sharp melting endotherm with a signal maximum at about 168° C. and a heat of fusion of 75 J/g.

The endothermic transition of polymorph Form B to Form A indicates an enantiotropic relationship between the two forms, i.e. polymorph Form B is thermodynamically more stable below the transition temperature (about 148° C.) and polymorph Form A is thermodynamically more stable above the transition temperature. This follows from the heat of transition rule (cf. e.g. R. Hilfiker (ed.), "Polymorphism in the Pharmaceutical Industry", 2006, Wiley-VCH, Weinheim, Germany).

Formulation/Utility

A solid form of Compound 1 or a mixture (i.e. composition) comprising a solid form of Compound 1 with (b) at least one fungicidal compound selected from mixing partners described in the tables herein, will generally be used to provide fungicidal active ingredients in further compositions, i.e. formulations, with at least one additional component selected from the group consisting of surfactants, solid diluents and liquid carriers (i.e. liquid fluids that carry the active and possibly other ingredients; also called liquid diluents). The formulation or composition ingredients are selected to be consistent with the physical properties of the active ingredient, mode of application and environmental factors such as soil type, moisture and temperature.

The mixtures of component (a) (i.e. a solid form of Compound 1) with component (b) (e.g., selected from table A) and/or one or more other biologically active compounds or agents (c) (i.e. insecticides, other fungicides, nematocides, acaricides, herbicides and other biological agents) can be formulated in a number of ways, including:

(i) component (a), component (b) and optionally (c) one or more other biologically active compounds or agents can be formulated separately and applied separately or applied simultaneously in an appropriate weight ratio, e.g., as a tank mix; or (ii) component (a), component (b) and optionally (c) one or more other biologically active compounds or agents can be formulated together in the proper weight ratio.

Useful formulations generally include both liquid and solid compositions. Liquid compositions include solutions (e.g., emulsifiable concentrates), emulsions (including micro-emulsions), dispersions and suspensions, and combinations of these forms (e.g., suspo-emulsions). The term "suspension" particularly refers to a dispersion of particulates that has been stabilized by addition of a chemical additive to minimize or stop sedimentation of the active ingredient. In a dispersion or suspension of particulates (e.g., aqueous suspension concentrate and oil dispersion formulations), a liquid carrier forms a continuous liquid phase in which the particulates (e.g., of a solid form of Compound 1) are dispersed or suspended. In a composition that combines a suspension or dispersion of particulates with an emulsion containing a second (immiscible) liquid (e.g., a suspo-emulsion formulation), a liquid carrier forms a continuous liquid phase in which not only the particulates are suspended but also droplets (i.e. non-continuous liquid phase) of the second liquid are emulsified.

Dispersions and suspensions may be aqueous (i.e. containing mainly water as the liquid carrier) or non-aqueous (i.e., comprising water-immiscible organic compounds, commonly referred to as "oil", as the liquid carrier) according to the nature of the liquid carrier forming the continuous liquid phase. The general types of aqueous liquid compositions include soluble concentrates, suspension concentrates, capsule suspensions, concentrated emulsions, micro-emulsions and suspo-emulsions. Thus in suspo-emulsions the liquid carrier forming the continuous liquid phase is aqueous (i.e. contains water as its main constituent) and a water-immiscible liquid component is emulsified in the aqueous liquid carrier. The general types of non-aqueous liquid compositions include emulsifiable concentrates, micro-emulsifiable concentrates, dispersible concentrates and oil dispersions. Suspension concentrates contain particulates dispersed in a continuous liquid phase and exists as particulate dispersions on addition to water. Suspo-emulsions and oil dispersions form both particulate dispersions and emulsions that coexist on addition to water, where one or more of these phases may contain active ingredient. (In the present compositions, the particulate dispersions comprise a solid form of Compound 1.)

The general types of solid compositions include dusts, powders, granules, pellets, prills, pastilles, tablets, filled films (including seed coatings) and the like, which can be water-dispersible ("wettable") or water-soluble. Films and coatings formed from film-forming liquids are particularly useful for seed treatment, in addition to having applications in both liquid and solid formulation types in general. Active ingredients can be encapsulated (including micro-encapsulated) and further formed into a liquid suspension or dispersion or into a solid formulation, to protect the active ingredient or control or delay release of the active ingredient on application to the target. Alternatively, the entire formulation, including the active ingredient, can be encapsulated (or "overcoated"). Encapsulation can also control or delay release of the active ingredient. High-strength compositions can be prepared and used as intermediates for subsequent use in preparing lower strength liquid and solid formulations.

Of note is a composition embodiment wherein granules of a solid composition comprising a solid form of Compound 1 is mixed with granules of a solid composition comprising component (b). These mixtures can be further mixed with granules comprising one or more additional biologically active compounds or agents, e.g., additional agricultural protectants. Alternatively, two or more agricultural protectants (e.g., a component (a) a solid form of Compound 1, a component (b) compound, (c) an agricultural protectant other than component (a) or (b)) can be combined in the solid composition of one set of granules, which is then mixed with one or more sets of granules of solid compositions comprising one or more additional agricultural protectants. These granule mixtures can be in accordance with the general granule mixture disclosure of PCT Patent Publication WO 94/24861 or more preferably the homogeneous granule mixture teaching of U.S. Pat. No. 6,022,552.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

Although the solid forms of Compound 1 according to the present invention can be used to prepare liquid solutions, emulsifiable concentrates and emulsions by combining with a solvent dissolving the solid forms, the solid forms can only retain their identity in formulated compositions containing Compound 1 as a solid (e.g., particles). The fungicidal compositions of the present invention wherein the composition comprises at least one solid form of Compound 1 thus include liquid compositions containing Compound 1 as a solid (e.g., dispersions, suspensions, suspo-emulsions) and solid compositions of Compound 1.

Even though all polymorph forms and the amorphous solid form of Compound 1 can be used to prepare fungicidal compositions of the present invention, polymorph Form B is particularly useful for forming fungicidal compositions, especially liquid compositions, having excellent physical as well as chemical stability. Although all polymorph forms and the amorphous solid form of Compound 1 are relatively stable (metastable) when isolated and maintained near room temperature, they are nevertheless thermodynamically unstable relative to polymorph Form B. Therefore, they are inherently susceptible to conversion to polymorph Form B. Contact with moisture, subjection to higher temperatures or long time periods may promote conversion to a more stable crystal form. Contact with solvents generally also promotes conversion of crystal forms. Therefore liquid compositions comprising other polymorph forms, mixtures of polymorph forms or the amorphous solid form of Compound 1 are particularly vulnerable to spontaneous recrystallization to polymorph Form B. Because of minimal nucleation and slow growth, the polymorph Form B crystals formed will be relatively few and large. This can result in both decreased biological efficacy and increased settling of the active ingredient, because high biological activity and suspensibility depend upon small particle size of solid active ingredient dispersed in liquid compositions. Using polymorph Form B to prepare compositions for protecting a plant or plant seed from diseases caused by fungal pathogens removes the risk of later recrystallization in the compositions. Also, a formulation containing a less stable crystal form than Form B may change its biological activity over the course of its shelf life as the ratio of crystal forms change. This is generally highly undesired as required use rates (amount of active ingredient per hectare) would change unpredictably. Accordingly, of note is a composition for protecting a plant or plant seed from diseases caused by fungal pathogens of the invention comprising polymorph Form B of Compound 1.

Preparation Example 9 exemplifies an unstable formulation prepared from polymorph Form A. The example formulation could have resulted in decreased biological efficacy due to loss of the active fungicide in the sprayed formulation and/or clogging of application equipment due to large particle size of the growing and settling of solids.

Both liquid and solid formulations comprising at least one solid form of Compound 1 will typically contain effective amounts of active ingredient, solid diluent or liquid carrier, and surfactant within the following approximate ranges, which add up to 100 percent by weight. General ranges of amounts of active ingredient (i.e. a solid form of Compound 1 and optionally other active ingredients), diluent and surfactant components in the present composition comprising at least one solid form of Compound 1 are as follows:

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates;

phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as simple quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such as polyorganosiloxanes), sedimentation of active ingredients (suspending agents), viscosity (thixotropic or pseudoplastic thickeners), in-container microbial growth (antimicrobials), product freezing (antifreezes), color (dyes/pigment dispersions), wash-off (film formers or sticking agents), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The solid forms of Compound 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2000 µm can be wet milled using media mills to obtain particles with average diameters below 3 µm. Suspension concentrates and oil dispersions typically require an active ingredient particle size of 0.1 to 3 µm. Aqueous slurries can be made into finished suspension concentrates (see, for example, U.S. Pat. No. 3,060,084) or further processed by spray-drying to form water-dispersible granules. Dry formulations usually require dry milling processes (hammer or air milling), which produce average particle diameters in the 2 to 10 µm range. Particle size can be homogenized by applying an additional sieving step. Dusts and powders can be prepared by blending and grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pages 147-48; *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

A desirable particle size range for the technical solid form of Compound 1 is 100-300 µm for ease of handling during filtration and drying. The technical can then be milled, ground or sieved to the size needed for the desired formulation.

The particle size distribution of polymorph Form B can be determined using a laser diffraction particle size analyzer, optical light microscopy or analytical sieving. The particle size distribution parameters D10, D50 and D90 are defined, wherein D50 represents the median particle size of the distribution, i.e. 50% of the particles are smaller and 50% are larger than that size. Similarly, D90 indicates the particle size at which 90% of all particles are smaller than that size.

Particles of polymorph Form B of 4-(2-bromo-4-fluorophenyl)-N-(2-chloro-6-fluorophenyl)-1,3-dimethyl-1H-pyrazol-5-amine can be produced having a particle size distribution D90 of 500 µm or less or 480 µm or less, or 460 µm or less, or 440 µm or less, or 420 µm or less, or 400 µm or less, or 380 µm or less, or 360 µm or less, or 340 µm or less, or 320 µm or less, or 300 µm or less, or 280 µm or less, or 260 µm or less, or 240 µm or less, or 220 µm or less, or 200 µm or less, or 180 µm or less, or 160 µm or less, or 140 µm or less, or 120 µm or less, or 100 µm or less, or 80 µm or less, or 60 µm or less, or 40 µm or less, or 20 µm or less, or 10 µm or less, or 5 µm or less, or 1 µm or less.

Particles of polymorph Form B can be produced having a particle size distribution D50 of 400 µm or less, 380 µm or less, or 360 µm or less, or 340 µm or less, or 320 µm or less, or 300 µm or less, or 280 µm or less, or 260 µm or less, or 240 µm or less, or 220 µm or less, or 200 µm or less, or 180 µm or less, or 160 µm or less, or 140 µm or less, or 120 µm or less, or 100 µm or less, or 80 µm or less, or 70 µm or less, or 60 µm or less, or 50 µm or less, 45 µm or less, or 40 µm or less, or 35 µm or less, or 30 µm or less, or 25 µm or less, or 20 µm or less, or 15 µm or less, or 10 µm or less, or 5 µm or less, or 1 µm or less.

According to the United States Pharmacopeial Convention, the following parameters may be defined based on the cumulative distribution. QR(X)=cumulative distribution of particles with a dimension less than or equal to X (in µm) wherein R reflects the distribution type (e.g. 3 for volume).

Therefore Q3(X)=0.5 when X=$X_{50}$ (median particle dimension: 50% of particles are smaller and 50% of particles are larger).

Particles of polymorph Form B of 4-(2-bromo-4-fluorophenyl)-N-(2-chloro-6-fluorophenyl)-1,3-dimethyl-1H-pyrazol-5-amine can be produced having a cumulative distribution by volume basis Q3(X) (X in μm) of Q3(355) <0.50; or Q3(180) <0.50 and Q3(355) ≥0.50; or Q3(125) <0.50 and Q3(180) ≥0.50; or Q3(75) <0.50 and Q3(125) ≥0.50; or Q3(10) <0.50 and Q3(75) ≥0.50; or Q3(10) ≥0.50.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pages 81-96; Hance et al., *Weed Control Handbook*, 8th Ed., Blackwell Scientific Publications, Oxford, 1989; and *Developments in formulation technology*, PJB Publications, Richmond, UK, 2000.

Without further elaboration, it is believed that one skilled in the art using the preceding formulation description can utilize the present invention to its fullest extent. The following Examples of formulation are, therefore, to be construed as merely illustrative, and not limiting of the disclosure in any way whatsoever. Percentages are by weight, and all formulations are prepared in conventional ways.

Formulation Example A

| High Strength Concentrate | |
|---|---|
| polymorph Form B of Compound 1 | 98.5% |
| silica aerogel | 0.5% |
| synthetic amorphous fine silica | 1.0% |

Formulation Example B

| Wettable Powder | |
|---|---|
| polymorph Form B of Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Formulation Example C

| Granule | |
|---|---|
| polymorph Form B of Compound 1 | 10.0% |
| attapulgite granules (low volatile matter, 0.71/0.30 mm; U.S.S. No. 25-50 sieves) | 90.0% |

Formulation Example D

| Extruded Pellet | |
|---|---|
| polymorph Form B of Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Formulation Example E

| Emulsifiable Concentrate | |
|---|---|
| polymorph Form B of Compound 1 | 10.0% |
| polyoxyethylene sorbitol hexoleate | 20.0% |
| $C_6$-$C_{10}$ fatty acid methyl ester | 70.0% |

Formulation Example F

| Microemulsion | |
|---|---|
| polymorph Form B of Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Formulation Example G

| Seed Treatment | |
|---|---|
| polymorph Form B of Compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Formulation Example H

| Fertilizer Stick | |
|---|---|
| polymorph Form B of Compound 1 | 2.50% |
| pyrrolidone-styrene copolymer | 4.80% |
| tristyrylphenyl 16-ethoxylate | 2.30% |
| talc | 0.80% |
| corn starch | 5.00% |
| Nitrophoska ® Permanent 15-9-15 slow-release fertilizer (BASF) | 36.00% |
| kaolin | 38.00% |
| water | 10.60% |

Example I

| Suspension Concentrate | |
|---|---|
| polymorph Form B of Compound 1 | 35.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| polymorph Form B of Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| polymorph Form B of Compound 1 | 25.0% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| polymorph Form B of Compound 1 | 15.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Formulations are often diluted with water to form aqueous compositions before application. Aqueous compositions for direct applications to the plant or portion thereof (e.g., spray tank compositions) typically comprise at least about 1 ppm or more (e.g., from 1 ppm to 100 ppm) of fungicidally active compounds according to the present invention.

The compositions of this invention are useful as plant disease control agents. The present invention therefore further comprises a method for controlling plant diseases caused by fungal plant pathogens comprising applying to the plant or portion thereof to be protected, or to the plant seed or vegetative propagation unit to be protected, an effective amount of a composition of the invention (e.g., a composition comprising component (a), or components (a) and (b), or components (a), (b) and (c)). This aspect of the present invention can also be described as a method for protecting a plant or plant seed from diseases caused by fungal pathogens comprising applying a fungicidally effective amount of a composition of the invention to the plant (or portion thereof) or plant seed (directly or through the environment (e.g., growing medium) of the plant or plant seed).

Component (a) a solid form of Compound 1 with component (b) compounds and/or (c) one or more other biologically active compounds or agents can be applied to plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The solid forms of Compound 1 and their compositions may interact synergistically with traits introduced by genetic engineering or modified by mutagenesis, thus enhancing phenotypic expression or effectiveness of the traits or increasing the plant disease control effectiveness of the present compounds and compositions. In particular, the solid forms of Compound 1 and their compositions may interact synergistically with the phenotypic expression of proteins or other natural products toxic to fungal pathogens to provide greater-than-additive control of fungal disease.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Plant disease control is ordinarily accomplished by applying an effective amount of a composition of the invention (e.g., comprising component (a), or a mixture of components (a), (b) and optionally (c)), typically as a formulated composition, either pre- or post-infection, to the portion of the plant to be protected such as the roots, stems, foliage, fruit, seeds, tubers or bulbs, or to the media (soil or sand) in which the plants to be protected are growing. Component (a) or mixtures thereof can also be applied to seeds to protect the seeds and seedlings developing from the seeds. The mixtures can also be applied through irrigation water to treat plants. Control of postharvest pathogens which infect the produce before harvest is typically accomplished by field application of a composition of the invention, and in cases where infection occurs after harvest the compositions can be applied to the harvested crop as dips, sprays, fumigants, treated wraps or box liners.

Suitable rates of application (e.g., fungicidally effective amounts) of component (a) (i.e. a solid form of Compound 1) as well as suitable rates of application (e.g., biologically effective amounts, fungicidally effective amounts or insecticidally effective amounts) of components (b) and optionally (c) according to this invention can be influenced by many factors of the environment and should be determined under actual use conditions. Foliage can normally be protected when treated at a rate of from less than about 1 g/ha to about 5,000 g/ha of active ingredients. Seed and seedlings can normally be protected when seed is treated at a rate of from about 0.1 to about 10 g per kilogram of seed; and vegetative propagation units (e.g., cuttings and tubers) can normally be protected when propagation unit is treated at a rate of from about 0.1 to about 10 g per kilogram of propagation unit. One skilled in the art can easily determine through simple experimentation the application rates of component (a), and mixtures and compositions thereof, containing particular combinations of active ingredients according to this invention needed to provide the desired spectrum of plant protection and control of plant diseases and optionally other plant pests.

Solid forms of Compound 1, are particularly efficacious for controlling plant diseases caused by fungal pathogens, particularly in the Basidomycete and Ascomycete classes. Combining these compounds with other fungicidal compounds can provide control of diseases caused by a broad spectrum of fungal plant pathogens in the Basidiomycete, Ascomycete, Oomycete and Deuteromycete classes. Accordingly, mixtures and compositions described herein can control a broad spectrum of plant diseases, foliar pathogens of crops including: cereal grain crops such as wheat, barley, oats, rye, triticale, rice, maize, sorghum and millet; vine crops such as table and wine grapes; field crops such as oilseed rape (canola), sunflower; sugar beets, sugar cane, soybean, peanuts (groundnut), tobacco, alfalfa, clover, lespedeza, trefoil and vetch; pome fruits such as apple, pear, crabapple, loquat, mayhaw and quince; stone fruits such as peaches, cherries, plums, apricots, nectarines and almonds; citrus fruits such as lemons, limes, oranges, grapefruit, mandarin (tangerines) and kumquat; root and tuber vegetables and field crops (and their foliage) such as artichoke, garden and sugar beet, carrot, cassava, ginger, ginseng, horseradish, parsnip, potato, radish, rutabaga, sweet potato, turnip and yam; bulb vegetables such as garlic, leek, onion and shallot; leafy vegetables such as arugula (roquette), celery, celery, cress, endive (escarole), fennel, head and leaf lettuce, parsley, radicchio (red chicory), rhubarb, spinach and Swiss chard; brassica (cole) leafy vegetables such as broccoli, broccoli raab (rapini), Brussels sprouts, cabbage, bok Choy, cauliflower, collards, kale, kohlrabi, mustard and greens; legume vegetables (succulent or dried) such as lupin, bean (*Phaseolus* spp.) (including field bean, kidney bean, lima bean, navy bean, pinto bean, runner bean, snap bean, tepary bean and wax bean), bean (*Vigna* spp.) (including adzuki bean, asparagus bean, blackeyed pea, catjang, Chinese longbean, cowpea, crowder pea, moth bean, mung bean, rice bean, southern pea, urd bean and yardlong bean), broad bean (fava), chickpea (garbanzo), guar, jackbean, lablab bean, lentil and pea (*Pisum* spp.) (including dwarf pea, edible-podded pea, English pea, field pea, garden pea, green pea, snowpea, sugar snap pea, pigeon pea and soybean); fruiting vegetables such as eggplant, groundcherry (*Physalis* spp.), pepino and pepper (including bell pepper, chili pepper, cooking pepper, pimento, sweet pepper; tomatillo and tomato); cucurbit vegetables such as Chayote (fruit), Chinese waxgourd (Chinese preserving melon), citron melon, cucumber, gherkin, edible gourd (including hyotan, cucuzza, hechima, and Chinese okra), *Momordica* spp. (including balsam apple, balsam pear, bittermelon and Chinese cucumber), muskmelon (including cantaloupe and pumpkin), summer and winter squash (including butternut squash, calabaza, hubbard squash, acorn squash, spaghetti squash) and watermelon; berries such as blackberry (including bingleberry, boysenberry, dewberry, lowberry, marionberry, olallieberry and youngberry), blueberry, cranberry, currant, elderberry, gooseberry, huckleberry, loganberry, raspberry and strawberry; tree nuts such as almond, beech nut, Brazil nut, butternut, cashew, chestnut, chinquapin, filbert (hazelnut), hickory nut, macadamia nut, pecan and walnut; tropical fruits and other crops such as bananas, plantains, mangos, coconuts, papaya, guava, avocado, lichee, agave, coffee, cacao, sugar cane, oil palm, sesame, rubber and spices; fiber crops such as cotton, flax and hemp; turfgrasses (including warm- and cool-season turfgrasses) such as bentgrass, Kentucky bluegrass, St. Augustine grass, tall fescue and Bermuda grass.

These pathogens include: Oomycetes, including *Phytophthora* pathogens such as *Phytophthora infestans, Phytophthora megasperma, Phytophthora parasitica, Phytophthora cinnamomi* and *Phytophthora capsici, Pythium* pathogens such as *Pythium aphanidermatum*, and pathogens in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* pathogens such as *Alternaria solani* and *Alternaria brassicae, Guignardia* pathogens such as *Guignardia bidwelli, Venturia* pathogens such as *Venturia inaequalis, Septoria* pathogens such as *Septoria nodorum* and *Septoria tritici*, powdery mildew disease pathogens such as *Blumeria* spp. (including *Blumeria graminis*) and *Erysiphe* spp. (including *Erysiphe polygoni*), *Uncinula necatur, Sphaerotheca fuligena* and *Podosphaera leucotricha, Pseudocercosporella herpotrichoides, Botrytis* pathogens such as *Botrytis cinerea, Monilinia fructicola, Sclerotinia* pathogens such as *Sclerotinia sclerotiorum* and *Sclerotinia. minor, Magnaporthe grisea, Phomopsis viticola, Helminthosporium* pathogens such as *Helminthosporium tritici repentis, Pyrenophora teres*, anthracnose disease pathogens such as *Glomerella* or *Colletotrichum* spp. (such as *Colletotrichum graminicola* and *Colletotrichum orbicu-*

*lare*), and *Gaeumannomyces graminis*; Basidiomycetes, including rust diseases caused by *Puccinia* spp. (such as *Puccinia recondita, Puccinia striiformis, Puccinia hordei, Puccinia graminis* and *Puccinia arachidis*), *Hemileia vastatrix* and *Phakopsora pachyrhizi*; other pathogens including *Rhizoctonia* spp. (such as *Rhizoctonia solani* and *Rhizoctonia oryzae*); *Fusarium* pathogens such as *Fusarium roseum, Fusarium graminearum* and *Fusarium oxysporum; Verticillium dahliae; Sclerotium rolfsii; Rynchosporium secalis; Cercosporidium personatum, Cercospora arachidicola* and *Cercospora beticola; Rutstroemia floccosum* (also known as *Sclerontina homoeocarpa*); *Rhizopus* spp. (such as *Rhizopus stolonifer*); *Aspergillus* spp. (such as *Aspergillus flavus* and *Aspergillus parasiticus*); and other genera and species closely related to these pathogens. Commonly, pathogens are referred to as diseases, and thus in the preceding sentence the word "pathogen" also refers to the plant disease caused by the pathogen. More precisely, plant diseases are caused by pathogens. Therefore, for example, powdery mildew diseases are plant diseases caused by powdery mildew pathogens, *Septoria* diseases are plant diseases caused by *Septoria* pathogens, and rust diseases are plant diseases caused by rust disease pathogens. Certain fungicidal compounds are also bactericidal, and therefore in addition to their fungicidal activity, the compositions or combinations can also have activity against bacteria such as *Erwinia amylovora, Xanthomonas campestris, Pseudomonas syringae*, and other related species. Furthermore, solid forms of Compound 1 and their mixtures and compositions according to this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, application of compounds, mixtures and compositions according to this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g., fruits, seeds, foliage, stems, bulbs, tubers) can be stored refrigerated or unrefrigerated after harvest, and remain edible and free from noticeable or harmful degradation or contamination by fungi or other microorganisms. Treatment of edible plant parts before or after harvest with compounds, mixtures or compositions according to this invention can also decrease the formation of toxic metabolites of fungi or other microorganisms, for example, mycotoxins such as aflatoxins.

In the present fungicidal compositions, solid forms of Compound 1 of component (a) can work synergically with the additional fungicidal compounds of component (b) to provide such beneficial results as broadening the spectrum of plant diseases controlled, extending duration of preventative and curative protection, and suppressing proliferation of resistant fungal pathogens. In particular embodiments, compositions are provided in accordance with this invention that comprise proportions of component (a) and component (b) that are especially useful for controlling particular fungal diseases (such as *Alternaria solani, Blumeria graminis* f. sp. *tritici, Botrytis cinerea, Puccinia recondita* f. sp. *tritici, Rhizoctonia solani, Septoria nodorum, Septoria tritici*).

Mixtures of fungicides may also provide significantly better plant disease control than could be predicted based on the activity of the individual components. This synergism has been described as "the cooperative action of two components of a mixture, such that the total effect is greater or more prolonged than the sum of the effects of the two (or more) taken independently" (see P. M. L. Tames, *Neth. J. Plant Pathology* 1964, 70, 73-80). In methods providing plant disease control in which synergy is exhibited from a combination of active ingredients (e.g., fungicidal compounds) applied to the plant or seed, the active ingredients are applied in a synergistic weight ratio and synergistic (i.e. synergistically effective) amounts. Measures of disease control, inhibition and prevention cannot exceed 100%. Therefore expression of substantial synergism typically requires use of application rates of active ingredients wherein the active ingredients separately provide much less than 100% effect, so that their additive effect is substantially less than 100% to allow the possibility of an increase in effect as result of synergism. On the other hand, application rates of active ingredients that are too low may show not show much activity in mixtures even with the benefit of synergism. One skilled in the art can easily identify and optimize through simple experimentation the weight ratios and application rates (i.e. amounts) of fungicidal compounds providing synergy.

Solid forms of Compound 1 can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility.

Of note is a composition which, in addition to the solid forms of Compound 1 of component (a), includes as component (b) at least one fungicidal compound selected from the group consisting of the classes (b1) methyl benzimidazole carbamate (MBC) fungicides; (b2) dicarboximide fungicides; (b3) demethylation inhibitor (DMI) fungicides; (b4) phenylamide fungicides; (b5) amine/morpholine fungicides; (b6) phospholipid biosynthesis inhibitor fungicides; (b7) carboxamide fungicides; (b8) hydroxy(2-amino-)pyrimidine fungicides; (b9) anilinopyrimidine fungicides; (b10) N-phenyl carbamate fungicides; (b11) quinone outside inhibitor (QoI) fungicides; (b12) phenylpyrrole fungicides; (b13) quinoline fungicides; (b14) lipid peroxidation inhibitor fungicides; (b15) melanin biosynthesis inhibitors-reductase (MBI-R) fungicides; (b16) melanin biosynthesis inhibitors-dehydratase (MBI-D) fungicides; (b17) hydroxyanilide fungicides; (b18) squalene-epoxidase inhibitor fungicides; (b19) polyoxin fungicides; (b20) phenylurea fungicides; (b21) quinone inside inhibitor (QiI) fungicides; (b22) benzamide fungicides; (b23) enopyranuronic acid antibiotic fungicides; (b24) hexopyranosyl antibiotic fungicides; (b25) glucopyranosyl antibiotic: protein synthesis fungicides; (b26) glucopyranosyl antibiotic: trehalase and inositol biosynthesis fungicides; (b27) cyanoacetamideoxime fungicides; (b28) carbamate fungicides; (b29) oxidative phosphorylation uncoupling fungicides; (b30) organo tin fungicides; (b31) carboxylic acid fungicides; (b32) heteroaromatic fungicides; (b33) phosphonate fungicides; (b34) phthalamic acid fungicides; (b35) benzotriazine fungicides; (b36) benzene-sulfonamide fungicides; (b37) pyridazinone fungicides; (b38) thiophene-carboxamide fungicides; (b39) pyrimidinamide fungicides; (b40) carboxylic acid amide (CAA) fungicides; (b41) tetracycline antibiotic fungicides;

(b42) thiocarbamate fungicides; (b43) benzamide fungicides; (b44) host plant defense induction fungicides; (b45) multi-site contact activity fungicides; (b46) fungicides other than classes (b1) through (b45); and salts of compounds of classes (b1) through (b46).

Further descriptions of these classes of fungicidal compounds are provided below.

(b1) "Methyl benzimidazole carbamate (MBC) fungicides" (FRAC (Fungicide Resistance Action Committee) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(b2) "Dicarboximide fungicides" (FRAC code 2) are proposed to inhibit a lipid peroxidation in fungi through interference with NADH cytochrome c reductase. Examples include chlozolinate, iprodione, procymidone and vinclozolin.

(b3) "Demethylation inhibitor (DMI) fungicides" (FRAC code 3) inhibit C14-demethylase which plays a role in sterol production. Sterols, such as ergosterol, are needed for membrane structure and function, making them essential for the development of functional cell walls. Therefore, exposure to these fungicides result in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz, pefurazoate and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(b4) "Phenylamide fungicides" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl, metalaxyl-M (also known as mefenoxam). The oxazolidinones include oxadixyl. The butyrolactones include ofurace.

(b5) "Amine/morpholine fungicides" (FRAC code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(b6) "Phospholipid biosynthesis inhibitor fungicides" (FRAC code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(b7) "Carboxamide fungicides" (FRAC code 7) inhibit Complex II (succinate dehydrogenase) fungal respiration by disrupting a key enzyme in the Krebs Cycle (TCA cycle) named succinate dehydrogenase Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide and pyridine carboxamide. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include bixafen, furametpyr, isopyrazam, fluxapyroxad, sedaxane (N-[2-(1S,2R)-[1,1'-bicyclopropyl]-2-ylphenyl]-3-(difluoromethyl)-1-methyl-1H-pyrazole-4-carboxamide) and penflufen (N-[2-(1,3-dimethylbutyl)phenyl]-5-fluoro-1,3-dimethyl-1H-pyrazole-4-carboxamide (PCT Patent Publication WO 2003/010149)). The pyridine carboxamides include boscalid.

(b8) "Hydroxy(2-amino-)pyrimidine fungicides" (FRAC code 8) inhibit nucleic acid synthesis by interfering with adenosine deaminase. Examples include bupirimate, dimethirimol and ethirimol.

(b9) "Anilinopyrimidine fungicides" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(b10) "N-Phenyl carbamate fungicides" (FRAC code 10) inhibit mitosis by binding to β-tubulin and disrupting microtubule assembly Inhibition of microtubule assembly can disrupt cell division, transport within the cell and cell structure. Examples include diethofencarb.

(b11) "Quinone outside inhibitor (QoI) fungicides" (FRAC code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin and pyrametostrobin. The oximinoacetates include kresoxim-methyl, pyraoxystrobin and trifloxystrobin. The oximinoacetamides include dimoxystrobin, metominostrobin, orysastrobin, α-[methoxyimino]-N-methyl-2-[[[1-[3-(trifluoromethyl) phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide. The oxazolidinediones include famoxadone.

The dihydrodioxazines include fluoxastrobin. The imidazolinones include fenamidone. The benzylcarbamates include pyribencarb.

(b12) "Phenylpyrrole fungicides" (FRAC code 12) inhibit a MAP protein kinase associated with osmotic signal transduction in fungi. Fenpiclonil and fludioxonil are examples of this fungicide class.

(b13) "Quinoline fungicides" (FRAC code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

(b14) "Lipid peroxidation inhibitor fungicides" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazole fungicides include etridiazole.

(b15) "Melanin biosynthesis inhibitors-reductase (MBI-R) fungicides" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(b16) "Melanin biosynthesis inhibitors-dehydratase (MBI-D) fungicides" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(b17) "Hydroxyanilide fungicides (FRAC code 17) inhibit C4-demethylase which plays a role in sterol production. Examples include fenhexamid.

(b18) "Squalene-epoxidase inhibitor fungicides" (FRAC code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(b19) "Polyoxin fungicides" (FRAC code 19) inhibit chitin synthase. Examples include polyoxin.

(b20) "Phenylurea fungicides" (FRAC code 20) are proposed to affect cell division. Examples include pencycuron.

(b21) "Quinone inside inhibitor (QiI) fungicides" (FRAC code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(b22) "Benzamide fungicides" (FRAC code 22) inhibit mitosis by binding to β-tubulin and disrupting microtubule assembly Inhibition of microtubule assembly can disrupt cell division, transport within the cell and cell structure. Examples include zoxamide.

(b23) "Enopyranuronic acid antibiotic fungicides" (FRAC code 23) inhibit growth of fungi by affecting protein biosynthesis. Examples include blasticidin-S.

(b24) "Hexopyranosyl antibiotic fungicides" (FRAC code 24) inhibit growth of fungi by affecting protein biosynthesis. Examples include kasugamycin.

(b25) "Glucopyranosyl antibiotic: protein synthesis fungicides" (FRAC code 25) inhibit growth of fungi by affecting protein biosynthesis. Examples include streptomycin.

(b26) "Glucopyranosyl antibiotic: trehalase and inositol biosynthesis fungicides" (FRAC code 26) inhibit trehalase in inositol biosynthesis pathway. Examples include validamycin.

(b27) "Cyanoacetamideoxime fungicides (FRAC code 27) include cymoxanil.

(b28) "Carbamate fungicides" (FRAC code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(b29) "Oxidative phosphorylation uncoupling fungicides" (FRAC code 29) inhibit fungal respiration by uncoupling oxidative phosphorylation Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(b30) "Organo tin fungicides" (FRAC code 30) inhibit adenosine triphosphate (ATP) synthase in oxidative phosphorylation pathway. Examples include fentin acetate, fentin chloride and fentin hydroxide.

(b31) "Carboxylic acid fungicides" (FRAC code 31) inhibit growth of fungi by affecting deoxyribonucleic acid (DNA) topoisomerase type II (gyrase). Examples include oxolinic acid.

(b32) "Heteroaromatic fungicides" (FRAC code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(b33) "Phosphonate fungicides" (FRAC code 33) include phosphorous acid and its various salts, including fosetyl-aluminum.

(b34) "Phthalamic acid fungicides" (FRAC code 34) include teclofthalam.

(b35) "Benzotriazine fungicides" (FRAC code 35) include triazoxide.

(b36) "Benzene-sulfonamide fungicides" (FRAC code 36) include flusulfamide.

(b37) "Pyridazinone fungicides" (Fungicide Resistance Action Committee (FRAC) code 37) include diclomezine.

(b38) "Thiophene-carboxamide fungicides" (FRAC code 38) are proposed to affect ATP production. Examples include silthiofam.

(b39) "Pyrimidinamide fungicides" (FRAC code 39) inhibit growth of fungi by affecting phospholipid biosynthesis and include diflumetorim.

(b40) "Carboxylic acid amide (CAA) fungicides" (FRAC code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valifenalate (valiphenal). The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)-amino]butanamide and N-[2-[4-[[3-(4-chlorophenyl)-2-propyn-1-yl]oxy]-3-methoxyphenyl]-ethyl]-3-methyl-2-[(ethylsulfonyl)amino]butanamide.

(b41) "Tetracycline antibiotic fungicides" (FRAC code 41) inhibit growth of fungi by affecting complex 1 nicotinamide adenine dinucleotide (NADH) oxidoreductase. Examples include oxytetracycline.

(b42) "Thiocarbamate fungicides (b42)" (FRAC code 42) include methasulfocarb.

(b43) "Benzamide fungicides" (FRAC code 43) inhibit growth of fungi by delocalization of spectrin-like proteins. Examples include acylpicolide fungicides such as fluopicolide and fluopyram.

(b44) "Host plant defense induction fungicides" (FRAC code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

(b45) "Multi-site contact fungicides" inhibit fungal growth through multiple sites of action and have contact/preventive activity. This class of fungicides includes: (b45.1) "copper fungicides" (FRAC code M1)", (b45.2) "sulfur fungicides" (FRAC code M2), (b45.3) "dithiocarbamate fungicides" (FRAC code M3), (b45.4) "phthalimide fungicides" (FRAC code M4), (b45.5) "chloronitrile fungicides" (FRAC code M5), (b45.6) "sulfamide fungicides" (FRAC code M6), (b45.7) "guanidine fungicides" (FRAC code M7), (b45.8) "triazine fungicides" (FRAC code M8) and (b45.9) "quinone fungicides" (FRAC code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine and imoctadine, including iminoctadine albesilate and iminoctadine triacetate. "Triazine fungicides" include anilazine. "Quinone fungicides" include dithianon.

(b46) "Fungicides other than fungicides of classes (b1) through (b45)" include certain fungicides whose mode of action may be unknown. These include: (b46.1) "thiazole carboxamide fungicides" (FRAC code U5), (b46.2) "phenyl-acetamide fungicides" (FRAC code U6), (b46.3) "quinazolinone fungicides" (FRAC code U7) and (b46.4) "benzophenone fungicides" (FRAC code U8). The thiazole carboxamides include ethaboxam. The phenyl-acetamides include cyflufenamid and N-[[(cyclopropylmethoxy)amino] [6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone and pyriofenone. The (b46) class also includes bethoxazin, neo-asozin (ferric methanearsonate), fenpyrazamine, pyrrolnitrin, quinomethionate, tebufloquin, N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl] ethyl]-3-methyl-2-[(ethylsulfonyl)amino]-butanamide, 2-[[2-fluoro-5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl] methyl]propyl]carbamate, 5-chloro-6-(2,4,6-trifluorophenyl)-7-(4-methylpiperidin-1-yl) [1,2,4]triazolo[1,5-a]pyrimidine, N-(4-chloro-2-nitrophenyl)-N-ethyl-4-methylbenzenesulfonamide, N-[[(cyclopropylmethoxy)-amino][6-(difluoromethoxy)-2,3-difluorophenyl] methylene]benzeneacetamide, N'-[4-chloro-3-(trifluoromethyl)phenoxy]-2,5-dimethylphenyl]-N-ethyl-N-methylmethanimidamide and 1-[(2-propenylthio)carbonyl]-2-(1-methylethyl)-4-(2-methylphenyl)-5-amino-1H-pyrazol-3-one.

Therefore of note is a mixture (i.e. composition) comprising as component (a) a solid form of Compound 1 and as component (b) at least one fungicidal compound selected from the group consisting of the aforedescribed classes (b1) through (b46). Also of note are embodiments wherein component (b) comprises at least one fungicide from each of two different groups selected from (b1) through (b46). Also of note is a composition comprising said mixture (in fungicidally effective amount) and further comprising at least one additional component selected from the group consisting of surfactants, solid diluents and liquid diluents. Of particular note is a mixture (i.e. composition) comprising a solid form of Compound 1 and at least one fungicidal compound selected from the group of specific compounds listed above in connection with classes (b1) through (b46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are insecticides such as: abamectin, acephate, acetamiprid, acetoprole, aldicarb, amidoflumet (S-1955), amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorantraniliprole (DPX-E2Y45), chlorpyrifos, chlorpyrifos-methyl, chlorobenzilate, chromafenozide, clothianidin, cyantraniliprole (3-bromo-1-(3-chloro-2-pyridinyl)-N-[4-cyano-2-methyl-6-[(methylamino)-carbonyl]phenyl]-1H-pyrazole-5-carboxamide), cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim (UR-50701), flufenoxuron, fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron (XDE-007), noviflumuron, oxamyl, parathion, parathion-methyl, permethrin, phorate, phosalone, phosmet, phosphamidon, pirimicarb, profenofos, profluthrin, propargite, prothiocarb, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen (BSN 2060), spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon and triflumuron.

Additional examples of insecticides with which compounds of this invention can be formulated are: acequinocyl, acrinathrin, afidopyropen, benfuracarb, bensultap, borate, cadusafos, carbaryl, carzol, clofentezin, cyclaniliprole, cycloprothrin, cycloxaprid, cypermethrin, alpha-cypermethrin, zeta-cypermethrin, dimehypo, etofenprox, fenitrothion, flometoquin, flufenoxystrobin, flupiprole, flupyradifurone, fluvalinate, tau-fluvalinate, formetanate, fosthiazate, heptafluthrin, insecticidal soaps, meperfluthrin, methiodicarb, monofluorothrin, nicotine, pyflubumide, pyriminostrobin, silafluofen, spirodiclofen, sulfoxaflor, tetramethrin, tetramethylfluthrin, triflumezopyrim and 1-[(2-chloro-5-thiazolyl)methyl]-3-(3,5-dichlorophenyl)-2-hydroxy-9-methyl-4-oxo-4H-pyrido[1,2-a]pyrimidinium inner salt.

Examples of other biologically active compounds or agents with which compounds of this invention can be formulated are nematocides such as: aldicarb, imicyafos, oxamyl and fenamiphos. Additional examples of nematocides with which compounds of this invention can be formulated are: abamectin, cadusaphos, carbofuran, chloropicrin, dazomet, 1,3-dichloropropene, dimethyl disulfide, ethoprophos, fenamiphos, flufensulfone, fluopyram, fosthiazate, imicyafos, iprodione, metam (sodium and potassium), spirotetramat, terbufos, thiodicarb, tioxazafen and 8-chloro-N-[(2-chloro-5-methoxyphenyl)sulfonyl]-6-(trifluoromethyl)-imidazo[1,2-c]pyridine-2-carboxamide.

Examples of other biologically active compounds or agents with which compounds of this invention can be formulated are bactericides such as streptomycin; and acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad.

Examples of other biological agents with which compounds of this invention can be formulated are entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); root colonizing bacteria such as *Bacillus firmus*; nematode parasitic bacteria such as *Pasteuria nishizawae*; entomopathogenic fungi, such as green muscardine fungus; and entomopathogenic virus (both naturally occurring and genetically modified) including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the weight ratio of these various mixing partners (in total) to a solid form of Compound 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of fungal diseases controlled beyond the spectrum controlled by a solid form of Compound 1 alone.

Listed below in Table A are embodiments of specific compositions comprising a solid form of Compound 1 (polymorph Form B) and an additional fungicide.

TABLE A

| Component (b) | Typical Weight Ratio | More Typical Weight Ratio | Most Typical Weight Ratio | Illustrative Weight Ratio |
|---|---|---|---|---|
| acibenzolar-S-methyl | 2:1 to 1:180 | 1:1 to 1:60 | 1:1 to 1:18 | 1:4 |
| aldimorph | 30:1 to 1:3 | 10:1 to 1:1 | 7:1 to 1:1 | 3:1 |
| ametoctradin | 9:1 to 1:18 | 3:1 to 1:6 | 3:1 to 1:3 | 1:1 |
| amisulbrom | 6:1 to 1:18 | 2:1 to 1:6 | 1:1 to 1:6 | 1:2 |
| anilazine | 90:1 to 2:1 | 30:1 to 4:1 | 22:1 to 4:1 | 8:1 |
| azaconazole | 7:1 to 1:18 | 2:1 to 1:6 | 2:1 to 1:4 | 1:2 |
| azoxystrobin | 9:1 to 1:12 | 3:1 to 1:4 | 3:1 to 1:3 | 1:1 |
| benalaxyl | 4:1 to 1:18 | 1:1 to 1:6 | 1:1 to 1:6 | 1:2 |
| benalaxyl-M | 4:1 to 1:36 | 1:1 to 1:12 | 1:1 to 1:8 | 1:3 |
| benodanil | 18:1 to 1:6 | 6:1 to 1:2 | 4:1 to 1:2 | 2:1 |
| benomyl | 45:1 to 1:4 | 15:1 to 1:1 | 11:1 to 1:1 | 4:1 |
| benthiavalicarb or benthiavalicarb-isopropyl | 2:1 to 1:36 | 1:1 to 1:12 | 1:1 to 1:12 | 1:4 |
| bethoxazin | 150:1 to 1:36 | 50:1 to 1:12 | 15:1 to 2:1 | 5:1 |
| binapacryl | 150:1 to 1:36 | 50:1 to 1:12 | 15:1 to 2:1 | 5:1 |
| biphenyl | 150:1 to 1:36 | 50:1 to 1:12 | 15:1 to 2:1 | 5:1 |
| bitertanol | 15:1 to 1:5 | 5:1 to 1:2 | 3:1 to 1:2 | 1:1 |
| bixafen | 12:1 to 1:9 | 4:1 to 1:3 | 2:1 to 1:3 | 1:1 |
| blasticidin-S | 3:1 to 1:90 | 1:1 to 1:30 | 1:4 to 1:30 | 1:12 |
| boscalid | 18:1 to 1:6 | 6:1 to 1:2 | 4:1 to 1:2 | 2:1 |

TABLE A-continued

| Component (b) | Typical Weight Ratio | More Typical Weight Ratio | Most Typical Weight Ratio | Illustrative Weight Ratio |
|---|---|---|---|---|
| bromuconazole | 15:1 to 1:9 | 5:1 to 1:3 | 3:1 to 1:3 | 1:1 |
| bupirimate | 3:1 to 1:90 | 1:1 to 1:30 | 1:3 to 1:30 | 1:10 |
| captafol | 90:1 to 1:4 | 30:1 to 1:2 | 15:1 to 2:1 | 5:1 |
| captan | 90:1 to 1:4 | 30:1 to 1:2 | 15:1 to 2:1 | 5:1 |
| carbendazim | 45:1 to 1:4 | 15:1 to 1:2 | 11:1 to 2:1 | 4:1 |
| carboxin | 18:1 to 1:6 | 6:1 to 1:2 | 4:1 to 1:2 | 2:1 |
| carpropamid | 15:1 to 1:9 | 5:1 to 1:3 | 3:1 to 1:3 | 1:1 |
| chloroneb | 300:1 to 2:1 | 100:1 to 4:1 | 100:1 to 14:1 | 35:1 |
| chlorothalonil | 90:1 to 1:4 | 30:1 to 1:2 | 15:1 to 2:1 | 5:1 |
| chlozolinate | 45:1 to 1:2 | 15:1 to 2:1 | 11:1 to 2:1 | 4:1 |
| clotrimazole | 15:1 to 1:9 | 5:1 to 1:3 | 3:1 to 1:3 | 1:1 |
| copper salts such as Bordeaux mixture (tribasic copper sulfate), copper oxychloride, copper sulfate and copper hydroxide | 450:1 to 1:1 | 150:1 to 4:1 | 45:1 to 5:1 | 15:1 |
| cyazofamid | 4:1 to 1:18 | 1:1 to 1:6 | 1:1 to 1:6 | 1:2 |
| cyflufenamid | 1:1 to 1:90 | 1:2 to 1:30 | 1:2 to 1:24 | 1:6 |
| cymoxanil | 6:1 to 1:18 | 2:1 to 1:6 | 1:1 to 1:5 | 1:2 |
| cyproconazole | 4:1 to 1:18 | 1:1 to 1:6 | 1:1 to 1:6 | 1:2 |
| cyprodinil | 22:1 to 1:9 | 7:1 to 1:3 | 4:1 to 1:2 | 2:1 |
| dichlofluanid | 150:1 to 1:36 | 50:1 to 1:12 | 15:1 to 2:1 | 5:1 |
| diclocymet | 150:1 to 1:36 | 50:1 to 1:12 | 15:1 to 2:1 | 5:1 |
| diclomezine | 15:1 to 1:9 | 5:1 to 1:3 | 3:1 to 1:3 | 1:1 |
| dicloran | 150:1 to 1:36 | 50:1 to 1:12 | 15:1 to 2:1 | 5:1 |
| diethofencarb | 22:1 to 1:9 | 7:1 to 1:3 | 7:1 to 1:2 | 2:1 |
| difenoconazole | 4:1 to 1:36 | 1:1 to 1:12 | 1:1 to 1:12 | 1:3 |
| diflumetorim | 150:1 to 1:36 | 50:1 to 1:12 | 15:1 to 2:1 | 5:1 |
| dimethirimol | 3:1 to 1:90 | 1:1 to 1:30 | 1:3 to 1:30 | 1:8 |
| dimethomorph | 9:1 to 1:6 | 3:1 to 1:2 | 3:1 to 1:2 | 1:1 |
| dimoxystrobin | 9:1 to 1:18 | 3:1 to 1:6 | 2:1 to 1:4 | 1:1 |
| diniconazole | 3:1 to 1:36 | 1:1 to 1:12 | 1:1 to 1:8 | 1:3 |
| diniconazole M | 3:1 to 1:90 | 1:1 to 1:30 | 1:1 to 1:12 | 1:3 |
| dinocap | 7:1 to 1:9 | 2:1 to 1:3 | 2:1 to 1:3 | 1:1 |
| dithianon | 15:1 to 1:4 | 5:1 to 1:2 | 5:1 to 1:2 | 2:1 |
| dodemorph | 30:1 to 1:3 | 10:1 to 1:1 | 7:1 to 1:1 | 3:1 |
| dodine | 30:1 to 1:2 | 10:1 to 2:1 | 10:1 to 2:1 | 4:1 |
| edifenphos | 30:1 to 1:9 | 10:1 to 1:3 | 3:1 to 1:3 | 1:1 |
| enoxastrobin | 9:1 to 1:18 | 3:1 to 1:6 | 2:1 to 1:4 | 1:1 |
| epoxiconazole | 3:1 to 1:36 | 1:1 to 1:12 | 1:1 to 1:7 | 1:3 |
| etaconazole | 3:1 to 1:36 | 1:1 to 1:12 | 1:1 to 1:7 | 1:3 |
| ethaboxam | 7:1 to 1:9 | 2:1 to 1:3 | 2:1 to 1:3 | 1:1 |
| ethirimol | 30:1 to 1:3 | 10:1 to 1:1 | 7:1 to 1:1 | 3:1 |
| etridiazole | 30:1 to 1:9 | 10:1 to 1:3 | 7:1 to 1:2 | 2:1 |
| famoxadone | 9:1 to 1:18 | 3:1 to 1:6 | 2:1 to 1:4 | 1:1 |
| fenamidone | 6:1 to 1:18 | 2:1 to 1:6 | 2:1 to 1:4 | 1:1 |
| fenarimol | 3:1 to 1:90 | 1:1 to 1:30 | 1:2 to 1:24 | 1:7 |
| fenbuconazole | 3:1 to 1:30 | 1:1 to 1:10 | 1:1 to 1:10 | 1:3 |
| fenfuram | 18:1 to 1:6 | 6:1 to 1:2 | 4:1 to 1:2 | 1:1 |
| fenhexamid | 30:1 to 1:2 | 10:1 to 2:1 | 10:1 to 2:1 | 4:1 |
| fenoxanil | 150:1 to 1:36 | 50:1 to 1:12 | 15:1 to 1:1 | 4:1 |
| fenpiclonil | 75:1 to 1:9 | 25:1 to 1:3 | 15:1 to 2:1 | 5:1 |
| fenpropidin | 30:1 to 1:3 | 10:1 to 1:1 | 7:1 to 1:1 | 2:1 |
| fenpropimorph | 30:1 to 1:3 | 10:1 to 1:1 | 7:1 to 1:1 | 2:1 |
| fenpyrazamine | 100:1 to 1:100 | 10:1 to 1:10 | 3:1 to 1:3 | 1:1 |
| fentin salt such as the acetate, chloride or hydroxide | 15:1 to 1:9 | 5:1 to 1:3 | 3:1 to 1:3 | 1:1 |
| ferbam | 300:1 to 1:2 | 100:1 to 2:1 | 30:1 to 4:1 | 10:1 |
| ferimzone | 30:1 to 1:5 | 10:1 to 1:2 | 7:1 to 1:2 | 2:1 |
| fluazinam | 22:1 to 1:5 | 7:1 to 1:2 | 3:1 to 1:2 | 1:1 |
| fludioxonil | 7:1 to 1:12 | 2:1 to 1:4 | 2:1 to 1:4 | 1:1 |
| flumetover | 9:1 to 1:6 | 3:1 to 1:2 | 3:1 to 1:2 | 1:1 |
| flumorph | 9:1 to 1:18 | 3:1 to 1:6 | 3:1 to 1:3 | 1:1 |
| fluopicolide | 3:1 to 1:18 | 1:1 to 1:6 | 1:1 to 1:6 | 1:2 |
| fluopyram | 15:1 to 1:90 | 5:1 to 1:30 | 3:1 to 1:3 | 1:1 |
| fluoromide | 150:1 to 2:1 | 50:1 to 4:1 | 37:1 to 5:1 | 14:1 |
| fluoxastrobin | 4:1 to 1:18 | 1:1 to 1:6 | 1:1 to 1:6 | 1:2 |
| fluquinconazole | 4:1 to 1:12 | 1:1 to 1:4 | 1:1 to 1:4 | 1:2 |
| flusilazole | 15:1 to 1:9 | 5:1 to 1:3 | 3:1 to 1:3 | 1:1 |
| flusulfamide | 90:1 to 1:2 | 30:1 to 2:1 | 15:1 to 2:1 | 5:1 |
| flutianil | 7:1 to 1:36 | 2:1 to 1:12 | 1:1 to 1:6 | 1:2 |
| flutolanil | 18:1 to 1:6 | 6:1 to 1:2 | 4:1 to 1:2 | 1:1 |
| flutriafol | 4:1 to 1:12 | 1:1 to 1:4 | 1:1 to 1:4 | 1:2 |
| fluxapyroxad | 12:1 to 1:9 | 4:1 to 1:3 | 2:1 to 1:3 | 1:1 |
| folpet | 90:1 to 1:4 | 30:1 to 1:2 | 15:1 to 2:1 | 5:1 |
| fosetyl-aluminum | 225:1 to 2:1 | 75:1 to 5:1 | 30:1 to 5:1 | 12:1 |
| fuberidazole | 45:1 to 1:4 | 15:1 to 1:2 | 11:1 to 2:1 | 4:1 |

TABLE A-continued

| Component (b) | Typical Weight Ratio | More Typical Weight Ratio | Most Typical Weight Ratio | Illustrative Weight Ratio |
|---|---|---|---|---|
| furalaxyl | 15:1 to 1:45 | 5:1 to 1:15 | 1:1 to 1:6 | 1:2 |
| furametpyr | 150:1 to 1:36 | 50:1 to 1:12 | 15:1 to 2:1 | 5:1 |
| guazatine or iminoctadine | 150:1 to 1:36 | 50:1 to 1:12 | 15:1 to 2:1 | 5:1 |
| hexaconazole | 15:1 to 1:36 | 5:1 to 1:12 | 1:1 to 1:5 | 1:2 |
| hymexazol | 225:1 to 2:1 | 75:1 to 4:1 | 75:1 to 9:1 | 25:1 |
| imazalil | 7:1 to 1:18 | 2:1 to 1:6 | 1:1 to 1:5 | 1:2 |
| imibenconazole | 15:1 to 1:36 | 5:1 to 1:12 | 1:1 to 1:5 | 1:2 |
| iodocarb | 150:1 to 1:36 | 50:1 to 1:12 | 15:1 to 2:1 | 4:1 |
| ipconazole | 15:1 to 1:36 | 5:1 to 1:12 | 1:1 to 1:5 | 1:2 |
| iprobenfos | 150:1 to 1:36 | 50:1 to 1:12 | 15:1 to 2:1 | 5:1 |
| iprodione | 120:1 to 1:2 | 40:1 to 2:1 | 15:1 to 2:1 | 5:1 |
| iprovalicarb | 9:1 to 1:9 | 3:1 to 1:3 | 2:1 to 1:3 | 1:1 |
| isoprothiolane | 150:1 to 2:1 | 50:1 to 4:1 | 45:1 to 5:1 | 15:1 |
| isopyrazam | 12:1 to 1:9 | 4:1 to 1:3 | 2:1 to 1:3 | 1:1 |
| isotianil | 12:1 to 1:9 | 4:1 to 1:3 | 2:1 to 1:3 | 1:1 |
| kasugamycin | 7:1 to 1:90 | 2:1 to 1:30 | 1:2 to 1:24 | 1:7 |
| kresoxim-methyl | 7:1 to 1:18 | 2:1 to 1:6 | 2:1 to 1:4 | 1:1 |
| mancozeb | 180:1 to 1:3 | 60:1 to 2:1 | 22:1 to 3:1 | 7:1 |
| mandipropamid | 6:1 to 1:18 | 2:1 to 1:6 | 2:1 to 1:4 | 1:1 |
| maneb | 180:1 to 1:3 | 60:1 to 2:1 | 22:1 to 3:1 | 7:1 |
| mepanipyrim | 18:1 to 1:3 | 6:1 to 1:1 | 6:1 to 1:1 | 2:1 |
| mepronil | 7:1 to 1:36 | 2:1 to 1:12 | 1:1 to 1:6 | 1:2 |
| meptyldinocap | 7:1 to 1:9 | 2:1 to 1:3 | 2:1 to 1:3 | 1:1 |
| metalaxyl | 15:1 to 1:45 | 5:1 to 1:15 | 1:1 to 1:6 | 1:2 |
| metalaxyl-M | 7:1 to 1:90 | 2:1 to 1:30 | 1:1 to 1:12 | 1:4 |
| metconazole | 3:1 to 1:18 | 1:1 to 1:6 | 1:1 to 1:6 | 1:2 |
| methasulfocarb | 150:1 to 1:36 | 50:1 to 1:12 | 15:1 to 1:1 | 5:1 |
| metiram | 150:1 to 1:36 | 50:1 to 1:12 | 15:1 to 1:1 | 5:1 |
| metominostrobin | 9:1 to 1:12 | 3:1 to 1:4 | 3:1 to 1:3 | 1:1 |
| metrafenone | 6:1 to 1:12 | 2:1 to 1:4 | 2:1 to 1:4 | 1:1 |
| myclobutanil | 5:1 to 1:26 | 1:1 to 1:9 | 1:1 to 1:8 | 1:3 |
| naftifine | 150:1 to 1:36 | 50:1 to 1:12 | 15:1 to 2:1 | 5:1 |
| neo-asozin (ferric methanearsonate) | 150:1 to 1:36 | 50:1 to 1:12 | 15:1 to 2:1 | 5:1 |
| nuarimol | 15:1 to 1:9 | 5:1 to 1:3 | 3:1 to 1:3 | 1:1 |
| octhilinone | 150:1 to 1:36 | 50:1 to 1:12 | 15:1 to 1:1 | 4:1 |
| ofurace | 15:1 to 1:45 | 5:1 to 1:15 | 1:1 to 1:6 | 1:2 |
| orysastrobin | 9:1 to 1:12 | 3:1 to 1:4 | 3:1 to 1:3 | 1:1 |
| oxadixyl | 15:1 to 1:45 | 5:1 to 1:15 | 1:1 to 1:6 | 1:2 |
| oxolinic acid | 30:1 to 1:9 | 10:1 to 1:3 | 7:1 to 1:2 | 2:1 |
| oxpoconazole | 15:1 to 1:36 | 5:1 to 1:12 | 1:1 to 1:5 | 1:2 |
| oxycarboxin | 18:1 to 1:6 | 6:1 to 1:2 | 4:1 to 1:2 | 1:1 |
| oxytetracycline | 15:1 to 1:9 | 5:1 to 1:3 | 3:1 to 1:3 | 1:1 |
| pefurazoate | 150:1 to 1:36 | 50:1 to 1:12 | 15:1 to 2:1 | 5:1 |
| penconazole | 1:1 to 1:45 | 1:2 to 1:15 | 1:2 to 1:15 | 1:6 |
| pencycuron | 150:1 to 1:2 | 50:1 to 2:1 | 11:1 to 2:1 | 4:1 |
| penflufen | 12:1 to 1:9 | 4:1 to 1:3 | 2:1 to 1:3 | 1:1 |
| penthiopyrad | 12:1 to 1:9 | 4:1 to 1:3 | 2:1 to 1:3 | 1:1 |
| phosphorous acid and salts thereof | 150:1 to 1:36 | 50:1 to 1:12 | 15:1 to 2:1 | 6:1 |
| phthalide | 150:1 to 1:36 | 50:1 to 1:12 | 15:1 to 2:1 | 6:1 |
| picoxystrobin | 7:1 to 1:18 | 2:1 to 1:6 | 1:1 to 1:5 | 1:2 |
| piperalin | 15:1 to 1:9 | 5:1 to 1:3 | 3:1 to 1:3 | 1:1 |
| polyoxin | 15:1 to 1:9 | 5:1 to 1:3 | 3:1 to 1:3 | 1:1 |
| probenazole | 15:1 to 1:9 | 5:1 to 1:3 | 3:1 to 1:3 | 1:1 |
| prochloraz | 22:1 to 1:4 | 7:1 to 1:1 | 7:1 to 1:2 | 2:1 |
| procymidone | 45:1 to 1:3 | 15:1 to 1:1 | 11:1 to 2:1 | 4:1 |
| propamocarb or propamocarb-hydrochloride | 30:1 to 1:2 | 10:1 to 2:1 | 10:1 to 2:1 | 4:1 |
| propiconazole | 4:1 to 1:18 | 1:1 to 1:6 | 1:1 to 1:5 | 1:2 |
| propineb | 45:1 to 1:2 | 15:1 to 2:1 | 11:1 to 2:1 | 4:1 |
| proquinazid | 3:1 to 1:36 | 1:1 to 1:12 | 1:1 to 1:12 | 1:3 |
| prothiocarb | 9:1 to 1:18 | 3:1 to 1:6 | 3:1 to 1:3 | 1:1 |
| prothioconazole | 6:1 to 1:18 | 2:1 to 1:6 | 1:1 to 1:5 | 1:2 |
| pyraclostrobin | 9:1 to 1:18 | 3:1 to 1:6 | 2:1 to 1:4 | 1:1 |
| pyrametostrobin | 9:1 to 1:18 | 3:1 to 1:6 | 2:1 to 1:4 | 1:1 |
| pyraoxystrobin | 9:1 to 1:18 | 3:1 to 1:6 | 2:1 to 1:4 | 1:1 |
| pyrazophos | 150:1 to 1:36 | 50:1 to 1:12 | 15:1 to 1:1 | 4:1 |
| pyribencarb | 15:1 to 1:6 | 5:1 to 1:2 | 4:1 to 1:2 | 1:1 |
| pyrifenox | 15:1 to 1:9 | 5:1 to 1:3 | 3:1 to 1:3 | 1:1 |
| pyrimethanil | 30:1 to 1:6 | 10:1 to 1:2 | 3:1 to 1:2 | 1:1 |
| pyriofenone | 6:1 to 1:12 | 2:1 to 1:4 | 2:1 to 1:4 | 1:1 |
| pyroquilon | 15:1 to 1:9 | 5:1 to 1:3 | 3:1 to 1:3 | 1:1 |
| pyrrolnitrin | 150:1 to 1:36 | 50:1 to 1:12 | 15:1 to 2:1 | 5:1 |
| quinconazole | 4:1 to 1:12 | 1:1 to 1:4 | 1:1 to 1:4 | 1:2 |
| quinomethionate | 150:1 to 1:36 | 50:1 to 1:12 | 15:1 to 2:1 | 5:1 |
| quinoxyfen | 4:1 to 1:18 | 1:1 to 1:6 | 1:1 to 1:6 | 1:2 |
| quintozene | 150:1 to 1:36 | 50:1 to 1:12 | 15:1 to 2:1 | 5:1 |

TABLE A-continued

| Component (b) | Typical Weight Ratio | More Typical Weight Ratio | Most Typical Weight Ratio | Illustrative Weight Ratio |
|---|---|---|---|---|
| silthiofam | 7:1 to 1:18 | 2:1 to 1:6 | 2:1 to 1:4 | 1:1 |
| simeconazole | 15:1 to 1:36 | 5:1 to 1:12 | 1:1 to 1:5 | 1:2 |
| spiroxamine | 22:1 to 1:4 | 7:1 to 1:2 | 5:1 to 1:2 | 2:1 |
| streptomycin | 15:1 to 1:9 | 5:1 to 1:3 | 3:1 to 1:3 | 1:1 |
| sulfur | 300:1 to 3:1 | 100:1 to 9:1 | 75:1 to 9:1 | 25:1 |
| tebuconazole | 7:1 to 1:18 | 2:1 to 1:6 | 1:1 to 1:5 | 1:2 |
| tebufloquin | 100:1 to 1:100 | 10:1 to 1:10 | 3:1 to 1:3 | 1:1 |
| tecloftalam | 150:1 to 1:36 | 50:1 to 1:12 | 15:1 to 2:1 | 5:1 |
| tecnazene | 150:1 to 1:36 | 50:1 to 1:12 | 15:1 to 2:1 | 5:1 |
| terbinafine | 150:1 to 1:36 | 50:1 to 1:12 | 15:1 to 2:1 | 5:1 |
| tetraconazole | 15:1 to 1:36 | 5:1 to 1:12 | 1:1 to 1:5 | 1:2 |
| thiabendazole | 45:1 to 1:4 | 15:1 to 1:2 | 11:1 to 2:1 | 4:1 |
| thifluzamide | 15:1 to 1:9 | 5:1 to 1:3 | 3:1 to 1:3 | 1:1 |
| thiophanate | 45:1 to 1:3 | 15:1 to 2:1 | 11:1 to 2:1 | 4:1 |
| thiophanate-methyl | 45:1 to 1:3 | 15:1 to 2:1 | 11:1 to 2:1 | 4:1 |
| thiram | 150:1 to 1:2 | 50:1 to 2:1 | 37:1 to 5:1 | 14:1 |
| tiadinil | 12:1 to 1:9 | 4:1 to 1:3 | 2:1 to 1:3 | 1:1 |
| tolclofos-methyl | 150:1 to 1:2 | 50:1 to 2:1 | 37:1 to 5:1 | 14:1 |
| tolylfluanid | 150:1 to 1:36 | 50:1 to 1:12 | 15:1 to 2:1 | 5:1 |
| triadimefon | 15:1 to 1:36 | 5:1 to 1:12 | 1:1 to 1:5 | 1:2 |
| triadimenol | 15:1 to 1:36 | 5:1 to 1:12 | 1:1 to 1:5 | 1:2 |
| triarimol | 3:1 to 1:90 | 1:1 to 1:30 | 1:2 to 1:24 | 1:7 |
| triazoxide | 150:1 to 1:36 | 50:1 to 1:12 | 15:1 to 2:1 | 5:1 |
| tricyclazole | 15:1 to 1:9 | 5:1 to 1:3 | 3:1 to 1:3 | 1:1 |
| tridemorph | 30:1 to 1:3 | 10:1 to 1:1 | 7:1 to 1:1 | 2:1 |
| trifloxystrobin | 6:1 to 1:18 | 2:1 to 1:6 | 2:1 to 1:4 | 1:1 |
| triflumizole | 15:1 to 1:9 | 5:1 to 1:3 | 3:1 to 1:3 | 1:1 |
| triforine | 15:1 to 1:9 | 5:1 to 1:3 | 3:1 to 1:3 | 1:1 |
| trimorphamide | 45:1 to 1:9 | 15:1 to 1:3 | 7:1 to 1:2 | 2:1 |
| triticonazole | 15:1 to 1:36 | 5:1 to 1:12 | 1:1 to 1:5 | 1:2 |
| uniconazole | 15:1 to 1:36 | 5:1 to 1:12 | 1:1 to 1:5 | 1:2 |
| validamycin | 150:1 to 1:36 | 50:1 to 1:12 | 3:1 to 1:3 | 1:1 |
| valifenalate | 6:1 to 1:18 | 2:1 to 1:6 | 2:1 to 1:4 | 1:1 |
| vinclozolin | 120:1 to 1:2 | 40:1 to 2:1 | 15:1 to 2:1 | 6:1 |
| zineb | 150:1 to 1:2 | 50:1 to 2:1 | 37:1 to 5:1 | 14:1 |
| ziram | 150:1 to 1:2 | 50:1 to 2:1 | 37:1 to 5:1 | 14:1 |
| zoxamide | 6:1 to 1:18 | 2:1 to 1:6 | 2:1 to 1:4 | 1:1 |
| 5-chloro-6-(2,4,6-trifluorophenyl)-7-(4-methylpiperidin-1-yl)[1,2,4]triazolo[1,5-a]pyrimidine | 15:1 to 1:36 | 5:1 to 1:12 | 1:1 to 1:6 | 1:2 |
| N[2-[4-[[3-(4-chlorophenyl)-2-propyn-1-yl]oxy]-3-methoxyphenyl]ethyl]-3-methyl-2-[(methylsulfonyl)amino]butanamide | 6:1 to 1:18 | 2:1 to 1:6 | 2:1 to 1:4 | 1:1 |
| N-[2-[4-[[3-(4-chlorophenyl)-2-propyn-1-yl]oxy]-3-methoxyphenyl]ethyl]-3-methyl-2-[(ethylsulfonyl)amino]butanamide | 6:1 to 1:18 | 2:1 to 1:6 | 2:1 to 1:4 | 1:1 |
| 2-butoxy-6-iodo-3-propyl-4H-1-benzopyran-4-one | 3:1 to 1:36 | 1:1 to 1:12 | 1:1 to 1:12 | 1:3 |
| 3-[5-(4-chlorophenyl)-2,3-dimethyl-3-isoxazolidinyl]pyridine | 15:1 to 1:9 | 5:1 to 1:3 | 3:1 to 1:3 | 1:1 |
| N'-[4-[[3-[(4-chlorophenyl)methyl]-1,2,4-thiadiazol-5-yl]oxy]-2,5-dimethylphenyl]-N-ethyl-N-methylmethanimidamide | 20:1 to 1:20 | 8:1 to 1:8 | 3:1 to 1:3 | 1:1 |
| 4-fluorophenyl N-[1-[[[1-(4-cyanophenyl)-ethyl]sulfonyl]methyl]propyl]carbamate | 6:1 to 1:18 | 2:1 to 1:6 | 2:1 to 1:4 | 1:1 |
| N-[[(cyclopropylmethoxy)amino][6-(difluoromethoxy)-2,3-difluorophenyl]-methylene]benzeneacetamide | 1:1 to 1:90 | 1:2 to 1:30 | 1:2 to 1:24 | 1:7 |
| α-[methoxyimino]-N-methyl-2-[[[1-[3-(trifluoromethyl)phenyl]ethoxy]imino]-methyl]benzeneacetamide | 9:1 to 1:18 | 3:1 to 1:6 | 3:1 to 1:3 | 1:1 |
| N'-[4-[4-chloro-3-(trifluoromethyl)phenoxy]-2,5-dimethylphenyl]-N-ethyl-N-methylmethanimidamide | 15:1 to 1:18 | 5:1 to 1:6 | 3:1 to 1:3 | 1:1 |
| N-(4-chloro-2-nitrophenyl)-N-ethyl-4-methylbenzenesulfonamide | 15:1 to 1:18 | 5:1 to 1:6 | 3:1 to 1:3 | 1:1 |
| 2-[[[3-(2,6-dichlorophenyl)-1-methyl-2-propen-1-ylidene]amino]oxy]methyl]-α-(methoxyimino)-N-methylbenzeneacetamide | 9:1 to 1:18 | 3:1 to 1:6 | 3:1 to 1:3 | 1:1 |
| pentyl N-[4-[[[[(1-methyl-1H-tetrazol-5-yl)-phenylmethylene]amino]oxy]methyl]-2-thiazolyl]carbamate | 9:1 to 1:18 | 3:1 to 1:6 | 3:1 to 1:3 | 1:1 |

TABLE A-continued

| Component (b) | Typical Weight Ratio | More Typical Weight Ratio | Most Typical Weight Ratio | Illustrative Weight Ratio |
|---|---|---|---|---|
| 2-[(3-bromo-6-quinolinyl)oxy]-N-(1,1-dimethyl-2-butyn-1-yl)-2-(methylthio)acetamide | 5:1 to 1:22 | 2:1 to 1:8 | 2:1 to 1:4 | 1:1 |
| 2-[(3-ethynyl-6-quinolinyl)oxy]-N-[1-(hydroxymethyl)-1-methyl-2-propyn-1-yl]-2-(methylthio)acetamide | 5:1 to 1:22 | 2:1 to 1:8 | 2:1 to 1:4 | 1:1 |
| N-(1,1-dimethyl-2-butyn-1-yl)-2-[(3-ethynyl-6-quinolinyl)oxy]-2-(methylthio)acetamide | 5:1 to 1:22 | 2:1 to 1:8 | 2:1 to 1:4 | 1:1 |
| 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone | 1:1 to 1:90 | 1:2 to 1:30 | 1:2 to 1:18 | 1:6 |
| 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone | 1:1 to 1:90 | 1:2 to 1:30 | 1:2 to 1:18 | 1:6 |
| 1-[4-[4-[5-[(2,6-difluorophenoxy)methyl]-4,5-dihydro-3-isoxazolyl]-2-thiazolyl]-1-piperdinyl-2-[5-methyl-3-(trifluoromethyl)-1H-pyrazol-1-yl]ethanone | 1:1 to 1:90 | 1:2 to 1:30 | 1:2 to 1:18 | 1:6 |
| (2-chloro-6-fluorophenyl)methyl 2-[1-[2-[3,5-bis(difluoromethyl)-1H-pyrazol-1-yl]acetyl]-4-piperidinyl]-4-thiazolecarboxylate | 1:1 to 1:90 | 1:2 to 1:30 | 1:2 to 1:18 | 1:6 |
| (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate | 1:1 to 1:90 | 1:2 to 1:30 | 1:2 to 1:18 | 1:6 |
| [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]-carbonyl]-3-pyridinyl]oxy]methyl 2-methylpropanoate | 90:1 to 1:4 | 30:1 to 1:2 | 15:1 to 3:1 | 7:1 |
| (3S,6S,7R,8R)-3-[[[3-(acetyloxy)-4-methoxy-2-pyridinyl]carbonyl]amino]-6-methyl-4,9-dioxo-8-(phenylmethyl)-1,5-dioxonan-7-yl 2-methylpropanoate | 90:1 to 1:4 | 30:1 to 1:2 | 15:1 to 3:1 | 7:1 |
| (3S,6S,7R,8R)-3-[[[3-[(acetyloxy)methoxy]-4-methoxy-2-pyridinyl]carbonyl]amino]-6-methyl-4,9-dioxo-8-(phenylmethyl)-1,5-dioxonan-7-yl 2-methylpropanoate | 90:1 to 1:4 | 30:1 to 1:2 | 15:1 to 3:1 | 7:1 |
| (3S,6S,7R,8R)-3-[[[4-methoxy-3-[[(2-methylpropoxy)carbonyl]oxy]-2-pyridinyl]-carbonyl]amino]-6-methyl-4,9-dioxo-8-(phenylmethyl)-1,5-dioxonan-7-yl 2-methylpropanoate | 90:1 to 1:4 | 30:1 to 1:2 | 15:1 to 3:1 | 7:1 |
| N-[[3-(1,3-benzodioxol-5-ylmethoxy)-4-methoxy-2-pyridinyl]carbonyl-O-[2,5-dideoxy-3-O-(2-methyl-1-oxopropyl)-2-(phenylmethyl)-L-arabinonoyl]-L-serine, (1→4')-lactone | 90:1 to 1:4 | 30:1 to 1:2 | 15:1 to 3:1 | 7:1 |
| 5-fluoro-2-[(4-methylphenyl)methoxy]-4-pyrimidinamine | 20:1 to 1:20 | 5:1 to 1:5 | 3:1 to 1:3 | 1:1 |
| 5-fluoro-2-[(4-fluorophenyl)methoxy]-4-pyrimidinamine | 20:1 to 1:20 | 5:1 to 1:5 | 3:1 to 1:3 | 1:1 |
| 5,8-difluoro-N-[2-[3-methoxy-4-[[4-(trifluoromethyl)-2-pyridinyl]oxy]phenyl]-ethyl]-4-quinazolinamine | 40:1 to 1:10 | 10:1 to 1:3 | 5:1 to 1:2 | 1:1 |
| pentyl N-[6-[[[(Z)-[(1-methyl-1H-tetrazol-5-yl)phenylmethylene]amino]oxy]methyl]-2-pyridinyl]carbamate | 40:1 to 1:10 | 10:1 to 1:3 | 5:1 to 1:2 | 1:1 |
| 1,1-dimethylethyl N-[6-[[[(Z)-[(1-methyl-1H-tetrazol-5-yl)phenylmethylene]amino]oxy]-methyl]-2-pyridinyl]carbamate | 40:1 to 1:10 | 10:1 to 1:3 | 5:1 to 1:2 | 1:1 |
| 3-butyn-1-yl N-[6-[[[(Z)-[(1-methyl-1H-tetrazol-5-yl)phenylmethylene]amino]oxy]-methyl]-2-pyridinyl]carbamate | 40:1 to 1:10 | 10:1 to 1:3 | 5:1 to 1:2 | 1:1 |
| N-(3',4'-difluoro[1,1'-biphenyl]-2-yl)-3-(trifluoromethyl)-2-pyrazinecarboxamide | 20:1 to 1:20 | 5:1 to 1:5 | 3:1 to 1:3 | 1:1 |
| N-[2-(2,4-dichlorophenyl)-2-methoxy-1-methylethyl]-3-(difluoromethyl)-1-methyl-1H-pyrazole-4-carboxamide | 20:1 to 1:20 | 5:1 to 1:5 | 3:1 to 1:3 | 1:1 |
| 3-(difluoromethyl)-N-[4-fluoro-2-(1,1,2,3,3,3-hexafluoropropoxy)phenyl]-1-methyl-1H-pyrazole-4-carboxamide | 20:1 to 1:20 | 5:1 to 1:5 | 3:1 to 1:3 | 1:1 |

TABLE A-continued

| Component (b) | Typical Weight Ratio | More Typical Weight Ratio | Most Typical Weight Ratio | Illustrative Weight Ratio |
|---|---|---|---|---|
| 3-(difluoromethyl)-1-methyl-N-[2-(1,1,2,2-tetrafluoroethoxy)phenyl]-1H-pyrazole-4-carboxamide | 20:1 to 1:20 | 5:1 to 1:5 | 3:1 to 1:3 | 1:1 |
| isofetamid | 20:1 to 1:20 | 5:1 to 1:5 | 3:1 to 1:3 | 1:1 |
| tolprocarb | 20:1 to 1:20 | 5:1 to 1:5 | 3:1 to 1:3 | 1:1 |
| (αR)-2-[(2,5-dimethylphenoxy)methyl]-α-methoxy-N-methylbenzeneacetamide | 20:1 to 1:20 | 5:1 to 1:5 | 3:1 to 1:3 | 1:1 |
| 2,6-dimethyl-1H,5H-[1,4]dithiino[2,3-c:5,6-c']dipyrrole-1,3,5,7(2H,6H)-tetrone | 1:1 to 1:400 | 1:4 to 1:100 | 1:8 to 1:50 | 1:1 |
| 1-[[(2S,3R)-3-(2-chlorophenyl)-2-(2,4-difluorophenyl)-2-oxiranyl]methyl]-1H-1,2,4-triazole | 36:1 to 1:30 | 12:1 to 1:10 | 6:1 to 1:4 | 1:1 |
| 2-[[(2S,3R)-3-(2-chlorophenyl)-2-(2,4-difluorophenyl)-2-oxiranyl]methyl]-1,2-dihydro-3H-1,2,4-triazole-3-thione | 36:1 to 1:30 | 12:1 to 1:10 | 6:1 to 1:4 | 1:1 |
| 1-[[(2S,3R)-3-(2-chlorophenyl)-2-(2,4-difluorophenyl)-2-oxiranyl]methyl]-5-(2-propen-1-ylthio)-1H-1,2,4-triazole | 36:1 to 1:30 | 12:1 to 1:10 | 6:1 to 1:4 | 1:1 |
| α-[3-(4-chloro-2-fluorophenyl)-5-(2,4-difluorophenyl)-4-isoxazolyl]-3-pyridinemethanol | 36:1 to 1:30 | 12:1 to 1:10 | 6:1 to 1:4 | 1:1 |
| (αS)-[3-(4-chloro-2-fluorophenyl)-5-(2,4-difluorophenyl)-4-isoxazolyl]-3-pyridinemethanol | 36:1 to 1:30 | 12:1 to 1:10 | 6:1 to 1:4 | 1:1 |
| (αR)-[3-(4-chloro-2-fluorophenyl)-5-(2,4-difluorophenyl)-4-isoxazolyl]-3-pyridinemethanol | 36:1 to 1:30 | 12:1 to 1:10 | 6:1 to 1:4 | 1:1 |
| 3-[2-[3-(4-chloro-2-fluorophenyl)-5-(2,4-difluorophenyl)-4-isoxazolyl]-2-oxiranyl]pyridine | 36:1 to 1:30 | 12:1 to 1:10 | 6:1 to 1:4 | 1:1 |
| 2-ethyl-3,7-dimethyl-6-[4-(trifluoromethoxy)phenoxy]-4-quinolinyl methyl carbonate | 36:1 to 1:30 | 12:1 to 1:10 | 6:1 to 1:4 | 1:1 |
| α-[2-chloro-4-(4-chlorophenoxy)phenyl]-α-ethyl-1H-1,2,4-triazole-1-ethanol | 36:1 to 1:30 | 12:1 to 1:10 | 6:1 to 1:4 | 1:1 |
| α-[2-chloro-4-(4-chlorophenoxy)phenyl]-α-(1H-1,2,4-triazol-1-ylmethyl)-1H-1,2,4-triazole-1-ethanol | 36:1 to 1:30 | 12:1 to 1:10 | 6:1 to 1:4 | 1:1 |
| N-cyclopropyl-3-(difluoromethyl)-5-fluoro-1-methyl-N-[[(2-(1-methylethyl)phenyl]methyl]-1H-pyrazole-4-carboxamide | 20:1 to 1:20 | 5:1 to 1:5 | 3:1 to 1:3 | 1:1 |
| N-[[5-chloro-2-(trifluoromethyl)phenyl]methyl]-N-cyclopropyl-3-(difluoromethyl)-5-fluoro-1-methyl-1H-pyrazole-4-carboxamide | 20:1 to 1:20 | 5:1 to 1:5 | 3:1 to 1:3 | 1:1 |
| N-[[2-chloro-6-(trifluoromethyl)phenyl]methyl]-N-cyclopropyl-3-(difluoromethyl)-5-fluoro-1-methyl-1H-pyrazole-4-carboxamide | 20:1 to 1:20 | 5:1 to 1:5 | 3:1 to 1:3 | 1:1 |
| N-[[3-chloro-2-fluoro-6-(trifluoromethyl)phenyl]methyl]-N-cyclopropyl-3-(difluoromethyl)-5-fluoro-1-methyl-1H-pyrazole-4-carboxamide | 20:1 to 1:20 | 5:1 to 1:5 | 3:1 to 1:3 | 1:1 |
| N-cyclopropyl-3-(difluoromethyl)-5-fluoro-1-methyl-N-[[5-methyl-2-(trifluoromethyl)phenyl]methyl]-1H-pyrazole-4-carboxamide | 20:1 to 1:20 | 5:1 to 1:5 | 3:1 to 1:3 | 1:1 |
| N-[[5-chloro-2-(1-methylethyl)phenyl]methyl]-N-cyclopropyl-3-(difluoromethyl)-5-fluoro-1-methyl-1H-pyrazole-4-carboxamide | 20:1 to 1:20 | 5:1 to 1:5 | 3:1 to 1:3 | 1:1 |
| N-cyclopropyl-N-[(2-cyclopropylphenyl)methyl]-3-(difluoromethyl)-5-fluoro-1-methyl-1H-pyrazole-4-carboxamide | 20:1 to 1:20 | 5:1 to 1:5 | 3:1 to 1:3 | 1:1 |
| N-cyclopropyl-3-(difluoromethyl)-N-[(2-ethyl-4,5-dimethylphenyl)methyl]-5-fluoro-1-methyl-1H-pyrazole-4-carboxamide | 20:1 to 1:20 | 5:1 to 1:5 | 3:1 to 1:3 | 1:1 |
| N-cyclopropyl-3-(difluoromethyl)-5-fluoro-N-[[5-fluoro-2-(1-methylethyl)phenyl]methyl-1-methyl-1H-pyrazole-4-carboxamide | 20:1 to 1:20 | 5:1 to 1:5 | 3:1 to 1:3 | 1:1 |
| 1,1-dimethylethyl in the 2-position, is (b6j) N-cyclopropyl-3-(difluoromethyl)-N-[[2-(1,1-dimethylethyl)phenyl]methyl]-5-fluoro-1-methyl-1H-pyrazole-4-carboxamide | 20:1 to 1:20 | 5:1 to 1:5 | 3:1 to 1:3 | 1:1 |
| N-cyclopropyl-3-(difluoromethyl)-N-[(2-ethyl-5-fluorophenyl)methyl]-5-fluoro-1-methyl-1H-pyrazole-4-carboxamide | 20:1 to 1:20 | 5:1 to 1:5 | 3:1 to 1:3 | 1:1 |

TABLE A-continued

| Component (b) | Typical Weight Ratio | More Typical Weight Ratio | Most Typical Weight Ratio | Illustrative Weight Ratio |
|---|---|---|---|---|
| N-cyclopropyl-N-[(2-cyclopropyl-5-fluoro-phenyl)methyl]-3-(difluoromethyl)-5-fluoro-1-methyl-1H-pyrazole-4-carboxamide | 20:1 to 1:20 | 5:1 to 1:5 | 3:1 to 1:3 | 1:1 |
| N-[(5-chloro-2-ethylphenyl)methyl]-N-cyclopropyl-3-(difluoromethyl)-5-fluoro-1-methyl-1H-pyrazole-4-carboxamide | 20:1 to 1:20 | 5:1 to 1:5 | 3:1 to 1:3 | 1:1 |
| N-cyclopropyl-3-(difluoromethyl)-5-fluoro-N-[[2-fluoro-6-(1-methylethyl)phenyl]methyl]-1-methyl-1H-pyrazole-4-carboxamide | 20:1 to 1:20 | 5:1 to 1:5 | 3:1 to 1:3 | 1:1 |
| N-cyclopropyl-3-(difluoromethyl)-5-fluoro-N-[[5-fluoro-2-(1-methylethyl)phenyl]methyl]-1-methyl-1H-pyrazole-4-carboxamide | 20:1 to 1:20 | 5:1 to 1:5 | 3:1 to 1:3 | 1:1 |
| N-[(2-cyclopentyl-5-fluorophenyl)methyl]-N-cyclopropyl-3-(difluoromethyl)-5-fluoro-1-methyl-1H-pyrazole-4-carboxamide | 20:1 to 1:20 | 5:1 to 1:5 | 3:1 to 1:3 | 1:1 |
| N'-[2,5-dimethyl-4-[[3-(1,1,2,2-tetrafluoro-ethoxy)phenyl]thio]phenyl]-N-ethyl-N-methylmethanimidamide | 20:1 to 1:20 | 5:1 to 1:5 | 3:1 to 1:3 | 1:1 |
| N'-[4-[[4-chloro-3-(1,1,2,2-tetrafluoro-ethoxy)phenyl]thio]-2,5-dimethylphenyl]-N-ethyl-N-methylmethanimidamide | 20:1 to 1:20 | 5:1 to 1:5 | 3:1 to 1:3 | 1:1 |
| N-ethyl-N'-[4-[[4-fluoro-3-(1,1,2,2-tetra-fluoroethoxy)phenyl]thio]-2,5-dimethyl-phenyl]-N-methylmethanimidamide | 20:1 to 1:20 | 5:1 to 1:5 | 3:1 to 1:3 | 1:1 |
| N'-[2,5-dimethyl-4-[3-[(1,1,2,2-tetrafluoro-ethyl)thio]phenoxy]phenyl]-N-ethyl-N-methylmethanimidamide | 20:1 to 1:20 | 5:1 to 1:5 | 3:1 to 1:3 | 1:1 |
| N'-[2,5-dimethyl-4-[4-chloro-3-[(1,1,2,2-tetrafluoroethyl)thio]phenoxy]phenyl]-N-ethyl-N-methylmethanimidamide | 20:1 to 1:20 | 5:1 to 1:5 | 3:1 to 1:3 | 1:1 |
| N'-[2,5-dimethyl-4-[4-fluoro-3-[(1,1,2,2-tetrafluoroethyl)thio]phenoxy]phenyl]-N-ethyl-N-methylmethanimidamide | 20:1 to 1:20 | 5:1 to 1:5 | 3:1 to 1:3 | 1:1 |
| N'-[2,5-dimethyl-4-[[3-[(1,1,2,2-tetrafluoroethyl)thio]phenyl]thio]phenyl]-N-ethyl-N-methylmethanimidamide | 20:1 to 1:20 | 5:1 to 1:5 | 3:1 to 1:3 | 1:1 |
| 2-[3,5-bis(difluoromethyl)-1H-pyrazol-1-yl]-1-[4-[4-[4,5-dihydro-5-[2-[(methylsulfonyl)oxy] phenyl]-3-isoxazolyl]-2-thiazolyl]-1-piperidinyl]ethanone | 400:1 to 1:1 | 100:1 to 4:1 | 50:1 to 8:1 | 1:1 |
| 2-[3,5-bis(difluoromethyl)-1H-pyrazol-1-yl]-1-[4-[4-[5-[2-fluoro-6-[(methylsulfonyl)-oxy]phenyl]-4,5-dihydro-3-isoxazolyl]-2-thiazolyl]-1-piperidinyl]ethanone | 400:1 to 1:1 | 100:1 to 4:1 | 50:1 to 8:1 | 1:1 |
| 2-[3,5-bis(difluoromethyl)-1H-pyrazol-1-yl]-1-[4-[4-[5-[2-chloro-6-[(methylsulfonyl)-oxy]phenyl]-4,5-dihydro-3-isoxazolyl]-2-thiazolyl]-1-piperidinyl]ethanone | 400:1 to 1:1 | 100:1 to 4:1 | 50:1 to 8:1 | 1:1 |
| 2-fluoro-6-[(8-fluoro-2-methyl-3-quinolinyl)-oxy]-α,α-dimethylbenzenemethanol | 40:1 to 1:10 | 10:1 to 1:3 | 5:1 to 1:2 | 1:1 |
| 2-[(7,8-difluoro-2-methyl-3-quinolinyl)oxy]-6-fluoro-α,α-dimethylbenzenemethanol | 40:1 to 1:10 | 10:1 to 1:3 | 5:1 to 1:2 | 1:1 |
| 9-fluoro-2,3-dihydro-2,2-dimethyl-5-(3-quinolinyl)-1,4-benzoxazepine | 40:1 to 1:10 | 10:1 to 1:3 | 5:1 to 1:2 | 1:1 |
| (1R,2S,5S)-rel-2-(chloromethyl)-5-[(4-chlorophenyl)methyl]-2-methyl-1-(1H-1,2,4-triazol-1-ylmethyl)cyclopentanol | 40:1 to 1:10 | 10:1 to 1:3 | 5:1 to 1:2 | 1:1 |
| 1-[[4-[(4-chlorophenyl)methyl]-1-methyl-6-oxabicyclo[3.2.0]hept-5-yl]methyl]-1H-1,2,4-triazole | 40:1 to 1:10 | 10:1 to 1:3 | 5:1 to 1:2 | 1:1 |
| 3-[(4-chlorophenyl)methyl]-2-hydroxy-2-(1H-1,2,4-triazol-1-ylmethyl)-1,1-cyclopentane-dimethanol | 40:1 to 1:10 | 10:1 to 1:3 | 5:1 to 1:2 | 1:1 |
| 3-(difluoromethyl)-N-(7-fluoro-2,3-dihydro-1,1,3-trimethyl-1H-inden-4-yl)-1-methyl-1H-pyrazole-4-carboxamide | 20:1 to 1:20 | 5:1 to 1:5 | 3:1 to 1:3 | 1:1 |
| 3-[(3,4-dichloro-5-isothiazolyl)methoxy]-1,2-benzisothiazole, 1,1-dioxide | 20:1 to 1:20 | 5:1 to 1:5 | 3:1 to 1:3 | 1:1 |
| 3-(difluoromethyl)-N-methoxy-1-methyl-N-[1-methyl-2-(2,4,6-trichlorophenyl)ethyl]-1H-pyrazole-4-carboxamide | 20:1 to 1:20 | 5:1 to 1:5 | 3:1 to 1:3 | 1:1 |
| methyl 5H-pyrrolo[3',4': 5,6][1,4]dithiino[2,3-c][1,2,5]thiadiazole-5,7(6H)-dione | 20:1 to 1:20 | 5:1 to 1:5 | 3:1 to 1:3 | 1:1 |
| 3-(4,4,5-trifluoro-3,4-dihydro-3,3-dimethyl-1-isoquinolinyl)quinoline | 20:1 to 1:20 | 5:1 to 1:5 | 3:1 to 1:3 | 1:1 |

TABLE A-continued

| Component (b) | Typical Weight Ratio | More Typical Weight Ratio | Most Typical Weight Ratio | Illustrative Weight Ratio |
|---|---|---|---|---|
| 3-(5-fluoro-3,4-dihydro-3,3,4,4-tetramethyl-1-isoquinolinyl)quinoline | 20:1 to 1:20 | 5:1 to 1:5 | 3:1 to 1:3 | 1:1 |
| 1,1-dimethylethyl N-[6-[[[(Z)-[(4,5-dihydro-4-methyl-5-oxo-1,2,4-oxadiazol-3-yl)-phenylmethylene]amino]oxy]methyl]-2-pyridinyl]carbamate | 40:1 to 1:10 | 10:1 to 1:3 | 5:1 to 1:2 | 1:1 |
| 3-butyn-1-yl N-[6-[[[(Z)-[(4,5-dihydro-4-methyl-5-oxo-1,2,4-oxadiazol-3-yl)phenylmethylene]amino]oxy]methyl]-2-pyridinyl]carbamate | 40:1 to 1:10 | 10:1 to 1:3 | 5:1 to 1:2 | 1:1 |

Listed below in Table B are embodiments of specific compositions comprising a solid form of Compound 1 (polymorph Form B) and an additional invertebrate pest control agent.

TABLE B

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |

TABLE B-continued

| Invertebrate Pest Control Agent | Mode of Action or Chemical Class | Typical Weight Ratio |
|---|---|---|
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Diseases caused by fungal pathogens are controlled in agronomic and nonagronomic applications by applying a solid form of Compound 1, typically in the form of a composition, in a biologically effective amount, to the environment of the fungal pathogens, including the agronomic and/or nonagronomic locus of disease, to the area to be protected, or directly on the fungal pathogens to be controlled.

Thus the present invention comprises a method for protecting a plant or plant seed from diseases caused by fungal pathogens in agronomic and/or nonagronomic applications, comprising applying to a plant or seed, or to the environment of the plant or seed a biologically effective amount of a solid form of Compound 1 or with a composition comprising at least one such compound or a composition comprising at least one such compound and at least one additional biologically active compound or agent. Examples of suitable compositions comprising a solid form of Compound 1 and at least one additional biologically active compound or agent include granular compositions wherein the additional active compound is present on the same granule as the compound of the invention or on granules separate from those of the compound of the invention.

Embodiments of the method of this invention include contacting the environment. Of note is the method wherein the environment is a plant. Also of note is the method wherein the environment is an animal. Also of note is the method wherein the environment is a seed.

To achieve contact with a solid form of Compound 1 or composition of the invention to protect a field crop from diseases caused by fungal pathogens, the solid form of Compound 1 or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Solid forms of Compound 1 can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for protecting a plant or plant seed from diseases caused by fungal pathogens comprising applying to a plant or seed, or to the environment of the plant or seed a biologically effective amount of a solid form of Compound 1 or with a composition comprising a biologically effective amount of a solid form of Compound 1. Of further note is that solid forms of Compound 1 are also effective by localized application to the locus of disease. Other methods of contact include application of a solid form of Compound 1 or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact involves a dimensionally stable fertilizer granule, stick or tablet comprising a solid form of Compound 1 or composition of the invention. The solid forms of Compound 1 can also be impregnated into building materials.

Solid forms of Compound 1 are also useful in seed treatments for protecting seeds from diseases caused by fungal pathogens. In the context of the present disclosure and claims, treating a seed means contacting the seed with a biologically effective amount of a solid form of Compound 1 which is typically formulated as a composition of the invention. This seed treatment protects the seed from diseases caused by fungal pathogens and generally can also protect roots and other plant parts in contact with the soil of the seedling developing from the germinating seed. The seed treatment may also provide protection of foliage by translocation of Compound 1 or a second active ingredient within the developing plant. Seed treatments can be applied to all types of seeds, including those from which plants genetically transformed to express specialized traits will germinate. Representative examples of genetically transformed plants include those expressing proteins toxic to parasitic nematodes, such as *Bacillus thuringiensis* toxin or those expressing herbicide resistance such as glyphosate acetyltransferase, which provides resistance to glyphosate.

One method of seed treatment is by spraying or dusting the seed with a solid form of Compound 1 (i.e. as a formulated composition) before sowing the seeds. Compositions formulated for seed treatment generally comprise a film former or adhesive agent. Therefore typically a seed coating composition of the present invention comprises a biologically effective amount of a solid form of Compound 1 and a film former or adhesive agent. Seed can be coated by spraying a flowable suspension concentrate directly into a tumbling bed of seeds and then drying the seeds. Alternatively, other formulation types such as wetted powders, solutions, suspo-emulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

Solid forms of Compound 1 and their compositions, both alone and in combination with other insecticides, nematicides, and fungicides, are particularly useful in seed treatment for crops including, but not limited to, maize or corn, soybeans, cotton, cereal (e.g., wheat, oats, barley, rye and rice), potatoes, vegetables and oilseed rape.

Other insecticides or nematicides with which solid forms of Compound 1 can be formulated to provide mixtures useful in seed treatment include but are not limited to abamectin, acetamiprid, acrinathrin, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

Fungicides with which solid forms of Compound 1 can be formulated to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Compositions comprising solid forms of Compound 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis, Pasteuria penetrans* and *Pasteuria nishizawae*. A suitable *Bacillus firmus* strain is strain CNCM 1-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by rhizobia bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The treated seed typically comprises a solid form of Compound 1 in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

Solid forms of Compound 1 can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as needed for application. Of note is a spray composition comprising a biologically effective amount of a solid form of Compound 1 or a composition thereof and a carrier. One embodiment of such a spray composition comprises a biologically effective amount of a solid form of Compound 1 or a composition thereof and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing.

Although a spray composition formed by diluting with water a sufficient concentration of the present fungicidal composition can provide sufficient efficacy for controlling fungal pathogens, separately formulated adjuvant products can also be added to spray tank mixtures. These additional adjuvants are commonly known as "spray adjuvants" or "tank-mix adjuvants", and include any substance mixed in a spray tank to improve the performance of a pesticide or alter the physical properties of the spray mixture. Adjuvants can be anionic or nonionic surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

The amount of adjuvants added to spray mixtures is generally in the range of about 2.5% to 0.1% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet® (Helena Chemical Company) polyalkyleneoxide modified heptamethyltrisiloxane and Assist® (BASF) 17% surfactant blend in 83% paraffin based mineral oil.

Nonagronomic uses refer to protecting a plant or plant seed from diseases caused by fungal pathogens in the areas other than fields of crop plants. Nonagronomic uses of the present compounds and compositions include control of diseases caused by fungal pathogens in stored grains, beans and other foodstuffs, and in textiles or building materials. Nonagronomic uses of the present solid forms and compositions also include control of fungal pathogens in ornamental plants, forests, in yards, along roadsides and railroad rights of way, and on turf such as lawns, golf courses and pastures. Nonagronomic uses of the present compounds and compositions also include fungal pathogen control in houses and other buildings which may be occupied by humans and/or companion, farm, ranch, zoo or other animals.

The solid forms of Compound 1 are also suitable for treatment of plant propagation material other than seed, such as fruit, tubers or plant seedlings. The propagation material can be treated with the compounds before planting, or the compounds can be applied to the planting site when the propagation material is being planted.

For agronomic applications, the rate of application required for effective control (i.e. "biologically effective amount") will depend on such factors as the particular fungal pathogen species to be controlled, the fungal life stage, the extent of disease, location, time of year, host crop, ambient moisture, temperature, and the like. Under normal circumstances, application rates of about 0.01 to 2 kg of active ingredients per hectare are sufficient to control diseases caused by fungal pathogens in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of control of diseases caused by fungal pathogens.

What is claimed is:

1. A polymorph of 4-(2-bromo-4-fluorophenyl)-N-(2-chloro-6-fluorophenyl)-1,3-dimethyl-1H-pyrazol-5-amine designated Form B characterized by a room-temperature powder Cu(Kα1)-X-ray diffraction pattern having at least the 2θ reflection positions

| 2θ |
|---|
| 10.894 |
| 15.361 |
| 16.134 |
| 17.718 |
| 20.322 |
| 24.285 |
| 25.84 |
| 27.54 |
| 29.449. |

2. A polymorph of 4-(2-bromo-4-fluorophenyl)-N-(2-chloro-6-fluorophenyl)-1,3-dimethyl-1H-pyrazol-5-amine designated Form A characterized by a room-temperature powder Cu(Kα1)-X-ray diffraction pattern having at least the 2θ reflection positions

| 2θ |
|---|
| 6.395 |
| 12.668 |
| 14.507 |
| 14.99 |
| 18.984 |
| 22.23 |
| 23.885 |
| 24.919 |
| 26.34. |

3. A method for preparing the polymorph Form B of claim 1 comprising forming a slurry with a solvent of one or more solid forms of 4-(2-bromo-4-fluorophenyl)-N-(2-chloro-6-fluorophenyl)-1,3-dimethyl-1H-pyrazol-5-amine selected from the group of Form A, amorphous forms and mixtures of any of the foregoing with Form B and maintaining the slurry while the solid forms of 4-(2-bromo-4-fluorophenyl)-N-(2-chloro-6-fluorophenyl)-1,3-dimethyl-1H-pyrazol-5-amine convert to polymorph Form B.

4. The method of claim 3 wherein the solid forms of 4-(2-bromo-4-fluorophenyl)-N-(2-chloro-6-fluorophenyl)-1,3-dimethyl-1H-pyrazol-5-amine comprises polymorph Form A.

5. The method of claim 3 wherein the solid forms of 4-(2-bromo-4-fluorophenyl)-N-(2-chloro-6-fluorophenyl)-1,3-dimethyl-1H-pyrazol-5-amine comprises a mixture of polymorphs Form A and Form B.

6. The method of claim 3 wherein seed crystals of polymorph Form B of claim 1 are added to the slurry.

7. The method of claim 3 wherein the slurry is agitated.

8. The method of claim 3 wherein the solvent comprises one or more of water, a $C_4$-$C_8$ ester, a $C_1$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

9. The method of claim 8 wherein the solvent comprises one or more of water or methanol.

10. A method for preparing the polymorph Form B of claim 1 comprising, (A) contacting 1-(2-bromo-4-fluorophenyl)-2-propanone and 1-chloro-3-fluoro-2-isothiocyanatobenzene in the presence of a first solvent to form a reaction mixture containing a thioamide intermediate, (B) optionally isolating the thioamide intermediate, (C) contacting the thioamide intermediate with methylhydrazine in the presence of a second solvent to form a reaction mixture containing 4-(2-bromo-4-fluorophenyl)-N-(2-chloro-6-fluorophenyl)-1,3-dimethyl-1H-pyrazol-5-amine, and (D) crystallizing the 4-(2-bromo-4-fluorophenyl)-N-(2-chloro-6-fluorophenyl)-1,3-dimethyl-1H-pyrazol-5-amine as the polymorph Form B.

11. The method of claim 10 wherein in step (D) Compound 1 is crystallized in the presence of seed crystals of polymorph Form B.

12. The method of claim 10 wherein in step (D) Compound 1 is crystallized in the presence of a third solvent and seed crystals of polymorph Form B.

13. The method of claim 12 wherein the third solvent comprises one or both of water or methanol.

14. A composition for protecting a plant or plant seed from diseases caused by fungal pathogens comprising (a) polymorph Form B of claim 1; and (b) at least one additional component selected from the group consisting of surfactants, solid diluents and liquid carriers.

15. A composition for protecting a plant or plant seed from diseases caused by fungal pathogens comprising (a) polymorph Form B of claim 1; and (b) at least one other nematocide, insecticide and/or fungicide.

16. A method for protecting a plant or plant seed from diseases caused by fungal pathogens comprising applying to a plant or seed, or to the environment of the plant or seed, a biologically effective amount of polymorph Form B of claim 1.

* * * * *